(12) United States Patent
Nakai et al.

(10) Patent No.: US 12,387,709 B2
(45) Date of Patent: Aug. 12, 2025

(54) COMPOSITION FOR ACOUSTIC LENS, ACOUSTIC LENS, ACOUSTIC WAVE PROBE, ULTRASOUND PROBE, ACOUSTIC WAVE MEASUREMENT APPARATUS, ULTRASOUND DIAGNOSTIC APPARATUS, PHOTOACOUSTIC WAVE MEASUREMENT APPARATUS AND ULTRASONIC ENDOSCOPE, AND METHOD FOR MANUFACTURING ACOUSTIC WAVE PROBE

(71) Applicant: FUJIFILM Corporation, Tokyo (JP)

(72) Inventors: Yoshihiro Nakai, Ashigarakami-gun (JP); Kazuhiro Hamada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 756 days.

(21) Appl. No.: 17/666,923

(22) Filed: Feb. 8, 2022

(65) Prior Publication Data

US 2022/0172701 A1 Jun. 2, 2022

Related U.S. Application Data

(63) Continuation of application No. PCT/JP2020/030767, filed on Aug. 13, 2020.

(30) Foreign Application Priority Data

Sep. 6, 2019 (JP) .................................. 2019-163019

(51) Int. Cl.
*G10K 11/30* (2006.01)
*C08K 3/22* (2006.01)
(Continued)

(52) U.S. Cl.
CPC ................ *G10K 11/30* (2013.01); *C08K 3/22* (2013.01); *C08K 9/00* (2013.01); *C08L 83/04* (2013.01);
(Continued)

(58) Field of Classification Search
CPC .. G10K 11/30; C08K 3/22; C08K 9/00; C08L 83/04
See application file for complete search history.

(56) References Cited

U.S. PATENT DOCUMENTS

| 2011/0142894 A1 | 6/2011 | Watanabe et al. |
| 2017/0252465 A1 | 9/2017 | Nagai et al. |
| 2018/0104384 A1 | 4/2018 | Nakai et al. |

FOREIGN PATENT DOCUMENTS

| CN | 102028637 A | 4/2011 |
| CN | 103694743 A | 4/2014 |

(Continued)

OTHER PUBLICATIONS

Monte, Salvatore Neoalkoxy Titanate and Zirconate Coupling Agent Additives in Thermoplastics. Polymers and Polymer Composites vol. 10, Issue 2. Feb. 2002, pp. 121-172. (Year: 2002).*
(Continued)

*Primary Examiner* — John E Uselding
(74) *Attorney, Agent, or Firm* — Sughrue Mion, PLLC

(57) ABSTRACT

A composition for an acoustic lens contains the following components (A) to (C):
(A) a polysiloxane having a vinyl group;
(B) a polysiloxane having two or more Si—H groups in a molecular chain thereof; and
(C) zinc oxide surface-treated with at least one surface treatment agent of an aminosilane compound, a mercaptosilane compound, an isocyanatosilane compound, a thiocyanatosilane compound, an aluminum alkoxide
(Continued)

compound, a zirconium alkoxide compound, or a titanium alkoxide compound, provided that the aminosilane compound does not have a Si—N—Si structure.

19 Claims, 1 Drawing Sheet

(51) Int. Cl.
  *C08K 9/00* (2006.01)
  *C08L 83/04* (2006.01)
  *A61B 8/00* (2006.01)
(52) U.S. Cl.
  CPC .... *A61B 8/4281* (2013.01); *C08K 2003/2296* (2013.01)

(56) References Cited

FOREIGN PATENT DOCUMENTS

| CN | 107005770 A | 8/2017 |
| EP | 3 318 193 A1 | 5/2018 |
| JP | 2017-012435 A | 1/2017 |
| JP | 2019-066818 A | 4/2019 |
| JP | 2019-072510 A | 5/2019 |
| WO | 2017/002746 A1 | 1/2017 |

OTHER PUBLICATIONS

Extended European Search Report dated Oct. 11, 2022, issued in European Application No. 20860593.1.

"Rubber Industry Raw Materials and Equipment Scriptchbook of Raw and Process Consumables", Rubber Industry Raw Materials and Equipment Scriptchbook, Ed. Beijing Polytechnic University Press, 1st Edition, Jan. 2019, pp. 1163-1164 (4 pages total).

Office Action dated Oct. 26, 2022 from the China National Intellectual Property Administration in CN Application No. 202080056951.4.

International Search Report dated Oct. 27, 2020, issued by the International Searching Authority in application No. PCT/JP2020/030767.

Written Opinion dated Oct. 27, 2020, issued by the International Searching Authority in application No. PCT/JP2020/030767.

International Preliminary Report on Patentability (with translation of Written Opinion) dated Mar. 8, 2022, issued by the International Bureau in application No. PCT/JP2020/030767.

* cited by examiner

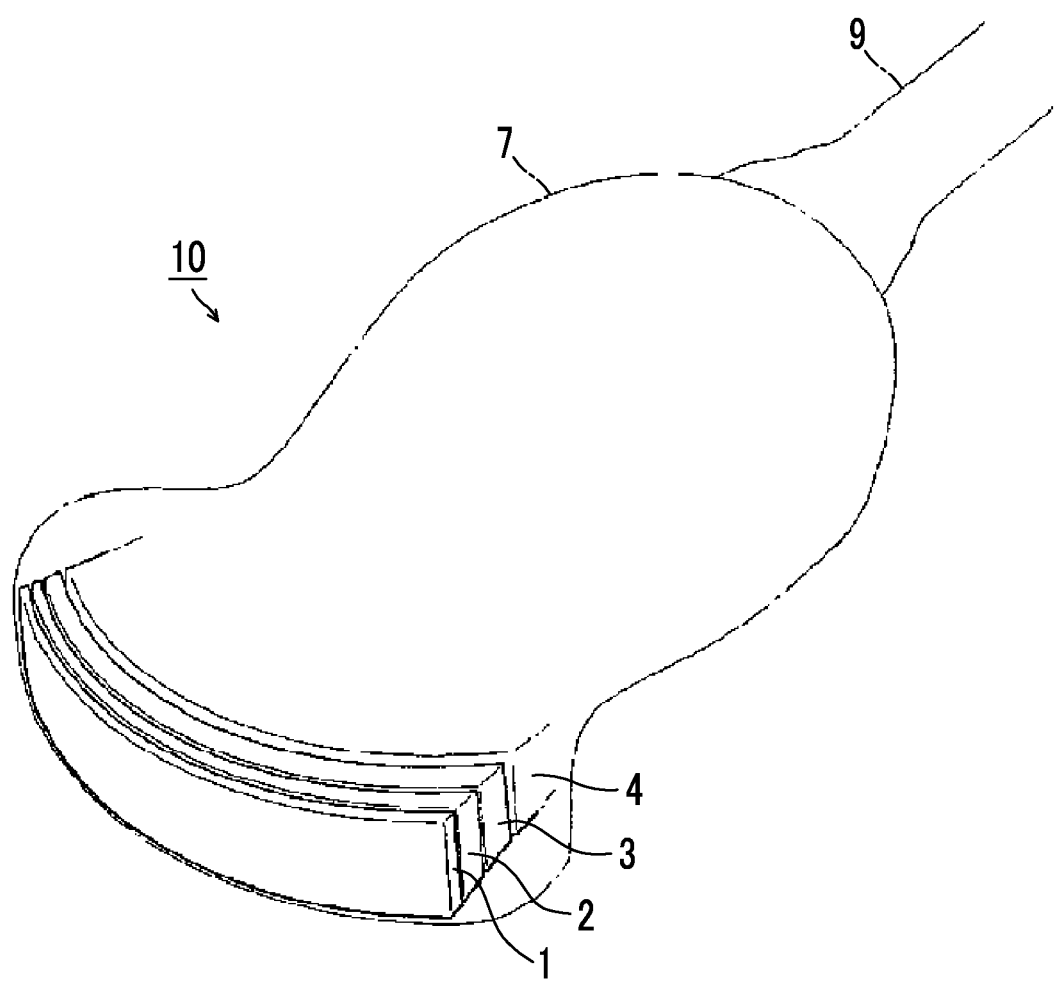

COMPOSITION FOR ACOUSTIC LENS, ACOUSTIC LENS, ACOUSTIC WAVE PROBE, ULTRASOUND PROBE, ACOUSTIC WAVE MEASUREMENT APPARATUS, ULTRASOUND DIAGNOSTIC APPARATUS, PHOTOACOUSTIC WAVE MEASUREMENT APPARATUS AND ULTRASONIC ENDOSCOPE, AND METHOD FOR MANUFACTURING ACOUSTIC WAVE PROBE

CROSS-REFERENCE TO RELATED APPLICATIONS

This application is a Continuation of PCT International Application No. PCT/JP2020/030767 filed on Aug. 13, 2020, which claims priority under 35 U.S.C. § 119(a) to Japanese Patent Application No. 2019-163019 filed on Sep. 6, 2019.

BACKGROUND OF THE INVENTION

1. Field of the Invention

The present invention relates to a composition for an acoustic lens, an acoustic lens, an acoustic wave probe, an ultrasound probe, an acoustic wave measurement apparatus, an ultrasound diagnostic apparatus, a photoacoustic wave measurement apparatus, an ultrasonic endoscope, and a method for manufacturing an acoustic wave probe.

2. Description of the Related Art

In an acoustic wave measurement apparatus, an acoustic wave probe is used which irradiates a test object or site (hereinafter, also referred to as "test object or the like") with an acoustic wave, receives a reflected wave (echo) therefrom, and outputs a signal. The electric signal converted from the reflected wave received by this acoustic wave probe is displayed as an image. As a result, the inside of the test object is visualized and observed.

As the acoustic wave, an ultrasonic wave, a photoacoustic wave, or the like having an appropriate frequency is selected according to the test object or the like or the measurement conditions or the like.

For example, an ultrasound diagnostic apparatus transmits an ultrasonic wave to the interior of a test object, receives the ultrasonic wave reflected by the tissues inside the test object, and displays the received ultrasonic wave as an image. The photoacoustic wave measurement apparatus receives an acoustic wave radiated from the interior of a test object due to a photoacoustic effect, and displays the received acoustic wave as an image. The photoacoustic effect is a phenomenon in which an acoustic wave (typically an ultrasonic wave) is generated through thermal expansion after a test object absorbs an electromagnetic wave to generate heat in a case where the test object is irradiated with an electromagnetic wave pulse of visible light, near infrared light, microwave, or the like.

Since an acoustic wave measurement apparatus transmits and receives an acoustic wave to and from a living body which is the test object, for example, the acoustic wave measurement apparatus is required to have matching of acoustic impedance with a living body (typically a human body), and is required to suppress the amount of acoustic wave attenuation. In addition, the acoustic wave measurement apparatus is also required to have a certain level of mechanical strength since it is used by rubbing it against a living body. In order to satisfy these requirements, a silicone resin is used as a resin material (base material) for an acoustic lens, and a mineral filler such as zinc oxide is formulated to adjust the acoustic impedance, mechanical strength, or the like.

For example, JP2019-72510A discloses a composition for an acoustic wave probe containing a polysiloxane mixture containing at least a polysiloxane having a vinyl group and a phenyl group, a polysiloxane having two or more Si—H groups in a molecular chain thereof, and zinc oxide; and a silicone resin for an acoustic wave probe obtained by curing the composition.

SUMMARY OF THE INVENTION

An acoustic wave measurement apparatus equipped with an acoustic wave probe is used not only for examining the inside of the body such as the abdomen and heart, but also for examining tissues near the body surface such as the mammary gland, thyroid gland, peripheral blood vessels, musculoskeletal system, nerves, and skin. The tissues near the body surface have a fine structure, and therefore a high-resolution examination image is required.

Generally, the resolution of an acoustic wave image increases as the frequency of an acoustic wave increases. Furthermore, lowering an acoustic velocity of an acoustic lens constituting the acoustic wave probe makes it possible to shorten a focal length and therefore to obtain a higher resolution image of the tissues near the body surface. That is, lowering the acoustic velocity of the acoustic lens makes it possible to obtain more accurate information about living tissues near the body surface.

Since this acoustic wave probe transmits and receives an acoustic wave by rubbing against a living body, peeling may occur between the acoustic lens and the acoustic matching layer, and this peeling causes the defocus of the acoustic wave image. The acoustic lens side (the portion in contact with the acoustic lens) of this acoustic matching layer is generally composed of an epoxy resin cured substance. Therefore, the acoustic lens needs to have characteristics of being hard to be peeled off from the epoxy resin cured substance constituting the acoustic matching layer.

The acoustic wave probe is not only applied from outside the living body, but is also used to examine the inside of the body more precisely by being inserted into the body cavity of the esophagus, stomach, intestine, bronchus, or the like after insertion thereof through a forceps port of an endoscope. The acoustic wave probe thus inserted into the body cavity is also required to obtain a high-resolution image near the surface layer of the body cavity. In addition, the acoustic wave probe inserted into the body cavity is also required to have durability against body fluids. For example, in a case where the inside of the wall surface of the esophagus, stomach, duodenum, or the like is examined with an acoustic wave probe, the acoustic wave probe is required to have durability against gastric acid.

An object of the present invention is to provide a composition for an acoustic lens which is capable of achieving an acoustic lens that has a low acoustic velocity, is less likely to be peeled off from an acoustic matching layer, and has excellent durability against body fluids; and an acoustic lens obtained by curing the composition.

Another object of the present invention is to provide an acoustic wave probe, an ultrasound probe, an acoustic wave measurement apparatus, an ultrasound diagnostic apparatus, a photoacoustic wave measurement apparatus, an ultrasonic endoscope, and a method for manufacturing an acoustic wave probe, each of which has the acoustic lens.

As a result of extensive studies in view of the foregoing objects, the present inventors have found that, in a case where a polysiloxane having a vinyl group and a polysiloxane having two or more Si—H groups are subjected to a curing reaction in the presence of zinc oxide treated with a specific surface treatment agent, the obtained silicone resin is capable of achieving a sufficiently reduced acoustic velocity, has excellent adhesiveness to an epoxy resin cured sheet, and exhibits excellent durability against strongly acidic body fluids such as gastric juice. The present invention has been completed based on these findings.

The foregoing objects of the present invention have been achieved by the following means.

<1>

A composition for an acoustic lens containing the following components (A) to (C).
(A) a polysiloxane having a vinyl group,
(B) a polysiloxane having two or more Si—H groups in a molecular chain thereof,
(C) zinc oxide surface-treated with at least one surface treatment agent of an aminosilane compound, a mercaptosilane compound, an isocyanatosilane compound, a thiocyanatosilane compound, an aluminum alkoxide compound, a zirconium alkoxide compound, or a titanium alkoxide compound.

In this regard, the aminosilane compound does not have a Si—N—Si structure.

<2>

The composition for an acoustic lens according to <1>, in which the surface treatment agent is at least one of the aminosilane compound, the mercaptosilane compound, the isocyanatosilane compound, the aluminum alkoxide compound, or the zirconium alkoxide compound.

<3>

The composition for an acoustic lens according to <1> or <2>, in which the surface treatment agent is at least one of the mercaptosilane compound, the isocyanatosilane compound, the aluminum alkoxide compound, or the zirconium alkoxide compound.

<4>

The composition for an acoustic lens according to any one of <1> to <3>, in which the surface treatment agent is at least one of the aluminum alkoxide compound or the zirconium alkoxide compound.

<5>

The composition for an acoustic lens according to any one of <1> to <4>, in which the aluminum alkoxide compound includes an aluminum alkoxide compound containing at least one of an acetonato structure or an acetato structure.

<6>

The composition for an acoustic lens according to any one of <1> to <5>, in which the aluminum alkoxide compound includes at least one compound represented by General Formula (1).

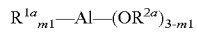  General Formula (1):

$R^{1a}$ represents a hydrogen atom, an alkyl group, a cycloalkyl group, an acyl group, an aryl group, or an unsaturated aliphatic group.

$R^{2a}$ represents a hydrogen atom, an alkyl group, a cycloalkyl group, an acyl group, an alkenyl group, an aryl group, a phosphonate group, or —SO$_2$R$^{S1}$. R$^{S1}$ represents a substituent.

m1 is an integer of 0 to 2.

<7>

The composition for an acoustic lens according to any one of <1> to <6>, in which the zirconium alkoxide compound includes a zirconium alkoxide compound containing at least one of an acetonato structure or an acetato structure.

<8>

The composition for an acoustic lens according to any one of <1> to <7>, in which the zirconium alkoxide compound includes at least one compound represented by General Formula (2).

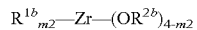  General Formula (2):

$R^{1b}$ represents a hydrogen atom, an alkyl group, a cycloalkyl group, an acyl group, an aryl group, or an unsaturated aliphatic group.

$R^{2b}$ represents a hydrogen atom, an alkyl group, a cycloalkyl group, an acyl group, an alkenyl group, an aryl group, a phosphonate group, or —SO$_2$R$^{S2}$. R$^{S2}$ represents a substituent.

m2 is an integer of 0 to 3.

<9>

The composition for an acoustic lens according to <1>, in which the titanium alkoxide compound includes a titanium alkoxide compound containing at least one atom of N, P, or S.

<10>

The composition for an acoustic lens according to <1> or <9>, in which the titanium alkoxide compound includes at least one compound represented by General Formula (3).

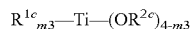  General Formula (3):

$R^{1c}$ represents a hydrogen atom, an alkyl group, a cycloalkyl group, an acyl group, an aryl group, or an unsaturated aliphatic group.

$R^{2c}$ represents a hydrogen atom, an alkyl group, a cycloalkyl group, an acyl group, an alkenyl group, an aryl group, a phosphonate group, or —SO$_2$R$^{S3}$. R$^{S3}$ represents a substituent.

m3 is an integer of 0 to 3.

<11>

The composition for an acoustic lens according to any one of <1> to <10>, in which a content of the surface treatment agent in the component (C) is 1 to 100 parts by mass with respect to 100 parts by mass of the zinc oxide.

<12>

The composition for an acoustic lens according to any one of <1> to <11>, in which an average primary particle diameter of the zinc oxide constituting the component (C) is 10 to 200 nm.

<13>

An acoustic lens obtained by curing the composition for an acoustic lens according to any one of <1> to <12>.

<14>

An acoustic wave probe having the acoustic lens according to <13>.

<15>

An ultrasound probe having the acoustic lens according to <13>.

<16>

An acoustic wave measurement apparatus including the acoustic wave probe according to <14>.

<17>

An ultrasound diagnostic apparatus including the acoustic wave probe according to <14>.

<18>

A photoacoustic wave measurement apparatus including the acoustic lens according to <13>.

<19>

An ultrasonic endoscope including the acoustic lens according to <13>.

<20>

A method for manufacturing an acoustic wave probe, including forming an acoustic lens using the composition for an acoustic lens according to any one of <1> to <12>.

In the description of the present specification, the "metal alkoxide compound (specifically, for example, a titanium alkoxide compound, an aluminum alkoxide compound, or a zirconium alkoxide compound which will be described later)" means a compound having a structure in which at least one alkoxy group is bonded to a metal atom. The alkoxy group may have a substituent. The substituent may be monovalent or divalent (for example, an alkylidene group). In addition, two alkoxy groups bonded to one metal atom may be bonded to each other to form a ring.

In the description of the present specification, unless otherwise specified, in a case where a plurality of groups having the same reference numerals are present in the general formula representing a compound, the groups may be the same or different from each other, and the group specified by each group (for example, an alkyl group) may further have a substituent. In addition, the "Si—H group" means a group having three bonding sites on the silicon atom, and the description of these bonding sites is omitted to simply the notation. Similarly, in the "Si—N—Si structure", each silicon atom has three bonding sites and the nitrogen atom has one bonding site.

In addition, the expression "to" in the present specification is used to mean that numerical values described before and after "to" are included as a lower limit value and an upper limit value, respectively.

The composition for an acoustic lens according to an aspect of the present invention is capable of achieving an acoustic lens that has a low acoustic velocity, is less likely to be peeled off from an acoustic matching layer, and has excellent durability against body fluids.

In addition, the acoustic lens according to the aspect of the present invention is suppressed to a low level of an acoustic velocity, is less likely to be peeled off from an acoustic matching layer, and has excellent durability against body fluids.

In addition, the acoustic wave probe, the ultrasound probe, the acoustic wave measurement apparatus, the ultrasound diagnostic apparatus, the photoacoustic wave measurement apparatus, and the ultrasonic endoscope according to the aspect of the present invention have the acoustic lens having excellent performance and produced by using the composition for an acoustic lens.

In addition, according to the method for manufacturing an acoustic wave probe according to the aspect of the present invention, an acoustic wave probe including the acoustic lens can be obtained.

BRIEF DESCRIPTION OF THE DRAWINGS

FIG. 1 is a perspective view of an example of a convex type ultrasound probe which is an aspect of an acoustic wave probe.

DESCRIPTION OF THE PREFERRED EMBODIMENTS

<<Composition for Acoustic Lens>>

The composition for an acoustic lens according to the embodiment of the present invention (hereinafter, also simply referred to as a composition) contains the following components (A) to (C).

(A) a polysiloxane having a vinyl group (component (A))
(B) a polysiloxane having two or more Si—H groups in a molecular chain thereof (component (B))
(C) zinc oxide surface-treated with at least one surface treatment agent of an aminosilane compound, a mercaptosilane compound, an isocyanatosilane compound, a thiocyanatosilane compound, an aluminum alkoxide compound, a zirconium alkoxide compound, or a titanium alkoxide compound (component (C))

In this regard, the aminosilane compound does not have a Si—N—Si structure. The reason for this will be described later.

As described above, the composition according to the embodiment of the present invention contains (A) a polysiloxane having a vinyl group (polyorganosiloxane) and (B) a polysiloxane having two or more Si—H groups in a molecular chain thereof. In this regard, (B) the polysiloxane having two or more Si—H groups in a molecular chain thereof is preferably (B) a polyorganosiloxane having two or more Si—H groups in a molecular chain thereof.

Therefore, the composition according to the embodiment of the present invention preferably contains at least the component (A), (B) the polyorganosiloxane (component (B)) having two or more Si—H groups in a molecular chain thereof, and the component (C).

The acoustic lens according to the embodiment of the present invention obtained by curing the composition according to the embodiment of the present invention having the above configuration has a low acoustic velocity, is less likely to be peeled off from an acoustic matching layer, and has excellent durability against corrosive body fluids such as gastric juice. The reasons for these effects are not clear yet, but it is presumed as follows.

It is presumed that, in a case where an acoustic lens contains a filler having large specific gravity; due to the inertia in a case where an acoustic wave (mainly a longitudinal wave) penetrates into the acoustic lens, the phase is delayed at a filler interface and therefore the acoustic velocity is lowered. It is considered that, since zinc oxide is surface-treated with a specific surface treatment agent, the component (C) contained in the acoustic lens according to the embodiment of the present invention is substantially uniformly dispersed in the lens using a silicone resin as a matrix to increase the phase delay and therefore effectively reduce the acoustic velocity. In addition, as described above, the acoustic lens side (the portion in contact with the acoustic lens) of this acoustic matching layer is generally composed of an epoxy resin cured substance. This epoxy resin cured substance has a hydroxyl group and is relatively hydrophilic. On the other hand, the silicone resin matrix constituting the acoustic lens according to the embodiment of the present invention is relatively hydrophobic. It is considered that the surface treatment agent (component derived therefrom) constituting the component (C) contained in the acoustic lens according to the embodiment of the present invention forms a covalent bond or a hydrogen bond with a polar group such as a hydroxyl group of the epoxy resin cured substance to improve the adhesiveness between the hydrophilic resin and the hydrophobic resin, whereby the acoustic lens is less likely to be peeled off from the acoustic matching layer. In addition, it is considered that the acoustic lens is excellent in durability against body fluids because the surface treatment agent itself is excellent in durability against body fluids.

In the following detailed description, the component (A) and (B) the polyorganosiloxane having two or more Si—H groups in a molecular chain thereof (component (B)), which are preferred aspects, will be described. However, the present invention is not limited to the aspects described below.

<(A) Polyorganosiloxane Having Vinyl Group (Component (A))>

The component (A) used in the present invention preferably has two or more vinyl groups in a molecular chain thereof.

The component (A) may be, for example, a polysiloxane (a1) having vinyl groups at least at both terminals of a molecular chain thereof (hereinafter, also simply referred to as component (a1)), or a polysiloxane (a2) having at least two —O—Si(CH$_3$)$_2$(CH=CH$_2$) in a molecular chain thereof excluding the terminals (hereinafter, also simply referred to as polysiloxane (a2)). Of these, the polysiloxane (a1) having vinyl groups at least at both terminals of a molecular chain thereof is preferable.

The polysiloxane (a2) is preferably a polysiloxane (a2) in which —O—Si(CH$_3$)$_2$(CH=CH$_2$) is bonded to a Si atom constituting a main chain.

The component (A) is hydrosilylated by the reaction with the component (B), for example, in the presence of a platinum catalyst. A crosslinking structure (cured body) can be formed by this hydrosilylation reaction (addition reaction).

The content of the vinyl group of the component (A) is not particularly limited. From the viewpoint of forming a sufficient network with each component contained in the composition for an acoustic lens, the content of the vinyl group is, for example, preferably 0.01 to 5 mol % and more preferably 0.05 to 2 mol %.

Here, the content of the vinyl group is mol % of the vinyl group-containing siloxane unit in a case where all the units constituting the component (A) are 100 mol %. One vinyl group-containing siloxane unit has one to three vinyl groups. Above all, the number of vinyl groups is preferably one for one vinyl group-containing siloxane unit. For example, in a case where all the Si atoms of the Si—O unit constituting the main chain and the terminal Si have at least one vinyl group, it amounts to 100 mol %.

The "unit" of polysiloxane refers to the Si—O unit constituting the main chain and the terminal Si.

In addition, the component (A) preferably has a phenyl group, and the content of the phenyl group of the polyorganosiloxane (A) is not particularly limited. From the viewpoint of mechanical strength in a case of being made into an acoustic lens, the content of the phenyl group is, for example, preferably 1 to 80 mol % and more preferably 2 to 40 mol %.

Here, the content of the phenyl group is mol % of the phenyl group-containing siloxane unit in a case where all the units constituting the component (A) are 100 mol %. One phenyl group-containing siloxane unit has one to three phenyl groups. Above all, the number of phenyl groups is preferably two for one phenyl group-containing siloxane unit. For example, in a case where all the Si atoms of the Si—O unit constituting the main chain and the terminal Si have at least one phenyl group, it amounts to 100 mol %.

A degree of polymerization and specific gravity are not particularly limited. From the viewpoint of improving the mechanical strength (tear strength) and chemical stability of the obtained acoustic lens, the viscosity of the composition before curing, and the like, the degree of polymerization is preferably 200 to 3,000 and more preferably 400 to 2,000, and the specific gravity is preferably 0.9 to 1.1.

The weight-average molecular weight of the component (A) is preferably 20,000 to 200,000, more preferably 40,000 to 150,000, and still more preferably 45,000 to 120,000, from the viewpoint of the mechanical strength of the acoustic lens and the viscosity of the composition before curing.

The weight-average molecular weight can be measured, for example, by using a gel permeation chromatography (GPC) device HLC-8220 (trade name, manufactured by Tosoh Corporation), toluene (manufactured by Shonan Wako Junyaku K.K.) as an eluent, TSKgel G3000HXL+TSKgel G2000HXL (both trade names, manufactured by Tosoh Corporation) as columns, and an RI (refractive index) detector under the conditions of a temperature of 23° C. and a flow rate of 1 mL/min.

The kinematic viscosity of the component (A) at 25° C. is preferably $1\times10^{-5}$ to 10 m$^2$/s, more preferably $1\times10^{-4}$ to 1 m$^2$/s, and still more preferably $1\times10^{-3}$ to 0.5 m$^2$/s.

The kinematic viscosity can be determined by measuring at a temperature of 25° C. using a Ubbelohde type viscometer (for example, SU: trade name, manufactured by Sibata Scientific Technology Ltd.) according to JIS Z8803.

The polyorganosiloxane (a1) having vinyl groups at least at both terminals of a molecular chain thereof is preferably a polyorganosiloxane represented by General Formula (A).

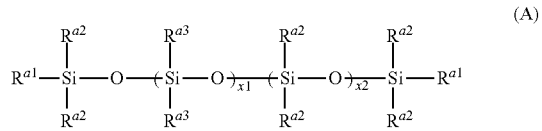

In General Formula (A), $R^{a1}$ represents a vinyl group, and $R^{a2}$ and $R^{a3}$ each independently represent an alkyl group, a cycloalkyl group, an alkenyl group, or an aryl group. x1 and x2 are each independently an integer of 1 or more.

The number of carbon atoms in the alkyl group for $R^{a2}$ and $R^{a3}$ is preferably 1 to 10, more preferably 1 to 4, still more preferably 1 or 2, and particularly preferably 1. Examples of the alkyl group include methyl, ethyl, propyl, isopropyl, butyl, isobutyl, hexyl, octyl, 2-ethylhexyl, and decyl.

The number of carbon atoms in the cycloalkyl group for $R^{a2}$ and $R^{a3}$ is preferably 3 to 10, more preferably 5 to 10, and still more preferably 5 or 6. In addition, the cycloalkyl group is preferably a 3-membered ring, a 5-membered ring, or a 6-membered ring, and more preferably a 5-membered ring or a 6-membered ring. Examples of the cycloalkyl group include cyclopropyl, cyclopentyl, and cyclohexyl.

The number of carbon atoms in the alkenyl group for $R^{a2}$ and $R^{a3}$ is preferably 2 to 10, more preferably 2 to 4, and still more preferably 2. Examples of the alkenyl group include vinyl, allyl, and butenyl.

The number of carbon atoms in the aryl group for $R^{a2}$ and $R^{a3}$ is preferably 6 to 12, more preferably 6 to 10, and still more preferably 6 to 8. Examples of the aryl group include phenyl, tolyl, and naphthyl.

The alkyl group, the cycloalkyl group, the alkenyl group, and the aryl group each may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include a halogenated alkyl group.

$R^{a2}$ and $R^{a3}$ are preferably an alkyl group, an alkenyl group, or an aryl group, more preferably an alkyl group having 1 to 4 carbon atoms, a vinyl group, or a phenyl group, still more preferably a methyl group, a vinyl group, or a phenyl group, and particularly preferably a methyl group or a phenyl group.

Above all, $R^{a2}$ is preferably a methyl group. Above all, $R^{a3}$ is preferably a methyl group, a vinyl group, or a phenyl group, more preferably a methyl group or a phenyl group, and particularly preferably a phenyl group.

x1 is preferably an integer of 200 to 3,000 and more preferably an integer of 400 to 2,000.

x2 is preferably an integer of 1 to 3,000, more preferably an integer of 1 to 1,000, still more preferably an integer of 40 to 1,000, and particularly preferably an integer of 40 to 700.

In addition, as another aspect, x1 is preferably an integer of 1 to 3,000 and more preferably an integer of 5 to 1,000.

In the present invention, repeating units "—Si($R^{a3}$)$_2$—O—" and "—Si(R)$_2$—O—" in General Formula (A) may each exist in a block-polymerized form or may be in a form that exists at random.

Examples of the polyorganosiloxane having vinyl groups at least at both terminals of a molecular chain thereof include DMS series (for example, DMS-V31, DMS-V31S15, DMS-V33, DMS-V35, DMS-V35R, DMS-V41, DMS-V42, DMS-V46, DMS-V51, and DMS-V52), PDV series (for example, PDV-0341, PDV-0346, PDV-0535, PDV-0541, PDV-1631, PDV-1635, PDV-1641, and PDV-2335), PMV-9925, PVV-3522, FMV-4031, and EDV-2022 (all trade names, manufactured by Gelest, Inc.).

The DMS-V31S15 is pre-formulated with fumed silica and therefore does not require kneading with a special device.

In the present invention, the component (A) may be used alone or in combination of two or more thereof.

<(B) Polysiloxane Having Two or More Si—H Groups in Molecular Chain Thereof (Component (B))>

The component (B) used in the present invention has two or more Si—H groups in a molecular chain thereof. Here, in a case where the component (B) has a "—SiH$_2$—" structure, the number of Si—H groups in the "—SiH$_2$—" structure is counted as two. In addition, in a case where the component (B) has a "—SiH$_3$" structure, the number of Si—H groups in the "—SiH$_3$" structure is counted as three.

Having two or more Si—H groups in the molecular chain makes it possible to crosslink a polyorganosiloxane having at least two polymerizable unsaturated groups.

The component (B) has a linear structure and a branched structure, among which a linear structure is preferable.

The weight-average molecular weight of the component (B) is preferably 500 to 100,000 and more preferably 1,500 to 50,000, from the viewpoint of the mechanical strength of the silicone resin and the viscosity of the composition before curing. The weight-average molecular weight of the component (B) can be measured in the same manner as the weight-average molecular weight of the component (A).

The component (B) having a linear structure is preferably a polyorganosiloxane represented by General Formula (B).

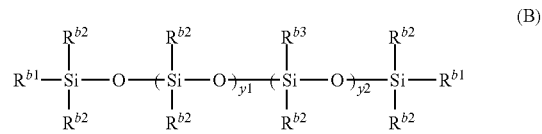

In General Formula (B), $R^{b1}$ to $R^{b3}$ each independently represent a hydrogen atom, an alkyl group, a cycloalkyl group, an alkenyl group, or an aryl group. y1 and y2 are each independently an integer of 1 or more. In this regard, the component (B) has two or more Si—H groups in a molecular chain thereof.

As an alkyl group, a cycloalkyl group, an alkenyl group, and an aryl group in $R^{b1}$ to $R^{b3}$, for example, an alkyl group, a cycloalkyl group, an alkenyl group, and an aryl group in Rae and $R^{a3}$ can be adopted.

$R^{b1}$ to $R^{b3}$ are each preferably a hydrogen atom, an alkyl group, an alkenyl group, or an aryl group, and more preferably a hydrogen atom, an alkyl group having 1 to 4 carbon atoms, a vinyl group, or a phenyl group.

Above all, $R^{b1}$ and $R^{b2}$ are each preferably a hydrogen atom, an alkyl group, an alkenyl group, or an aryl group, more preferably a hydrogen atom or an alkyl group, still more preferably a hydrogen atom or a methyl group, and particularly preferably a methyl group.

$R^{b3}$ is preferably a hydrogen atom, an alkyl group, an alkenyl group, or an aryl group, more preferably a hydrogen atom or an aryl group, still more preferably a hydrogen atom or a phenyl group, and particularly preferably a hydrogen atom.

y1 is preferably an integer of 0 to 2,000, more preferably an integer of 0 to 1,000, and still more preferably an integer of 0 to 30.

y2 is preferably an integer of 1 to 2,000, more preferably an integer of 1 to 1,000, and still more preferably an integer of 1 to 30.

y1+y2 is preferably an integer of 5 to 2,000, more preferably an integer of 7 to 1,000, still more preferably an integer of 10 to 50, and even still more preferably an integer of 15 to 30.

In the present invention, "—Si($R^{b2}$)$_2$—O—" and "—Si($R^{b2}$)($R^{b3}$)$_2$—O—" in General Formula (B) may each exist in a block-polymerized form in polysiloxane or may be in a form that exists at random.

The combination of $R^{b1}$ to $R^{b3}$ is preferably a combination of $R_{b1}$ being a hydrogen atom or an alkyl group having 1 to 4 carbon atoms, $R^{b2}$ being an alkyl group having 1 to 4 carbon atoms, and $R^{b3}$ being a hydrogen atom or an aryl group, and more preferably a combination of $R^{b1}$ being an alkyl group having 1 to 4 carbon atoms, $R^{b2}$ being an alkyl group having 1 to 4 carbon atoms, and $R^{b3}$ being a hydrogen atom or an aryl group.

In this preferred combination, the content of the hydrosilyl group represented by y2/(y1+y2) is preferably more than 0.1 and 1.0 or less, and more preferably more than 0.2 and 1.0 or less.

Examples of the component (B) having a linear structure include HMS-064 (MeHSiO: 5 to 7 mol %), HMS-082 (MeHSiO: 7 to 8 mol %), HMS-301 (MeHSiO: 25 to 30 mol %), and HMS-501 (MeHSiO: 50 to 55 mol %) as methylhydrosiloxane-dimethylsiloxane copolymers (trimethylsiloxane terminated), HPM-502 (MeHSiO: 45 to 50 mol %) as a methylhydrosiloxane-phenylmethylsiloxane copolymer, and HMS-991 (MeHSiO: 100 mol %) as a methylhydrosiloxane polymer, all of which are manufactured by Gelest, Inc.

Here, the mol % of MeHSiO has the same meaning as that y2/(y1+y2) in the preferred combination of $R^{b1}$ to $R^{b3}$ is multiplied by 100.

The component (B) having a branched structure has a branched structure and two or more hydrosilyl groups (Si—H groups).

The specific gravity thereof is preferably 0.9 to 0.95.

The component (B) having a branched structure is preferably represented by Average Composition Formula (b).

$$[H_a(R^{b6})_{3-a}SiO_{1/2}]_{y3}[SiO_{4/2}]_{y4} \quad \text{Average Composition Formula (b):}$$

Here, $R^{b6}$ represents an alkyl group, a cycloalkyl group, an alkenyl group, or an aryl group, a represents 0.1 to 3, and y3 and y4 each independently represent an integer of 1 or more.

As an alkyl group, a cycloalkyl group, an alkenyl group, and an aryl group in $R^{b6}$, for example, an alkyl group, a cycloalkyl group, an alkenyl group, and an aryl group in $R^{a2}$ and $R^{a3}$ can be adopted.

a is preferably 1.

The content of the hydrosilyl group represented by a/3 is preferably more than 0.1 and less than 0.6, and more preferably more than 0.1 and less than 0.4.

On the other hand, in a case where the component (B) having a branched structure is represented by a chemical structural formula, a polyorganosiloxane in which —O—Si(CH$_3$)$_2$(H) is bonded to a Si atom constituting a main chain is preferable, and a polyorganosiloxane having a structure represented by General Formula (Bb) is more preferable.

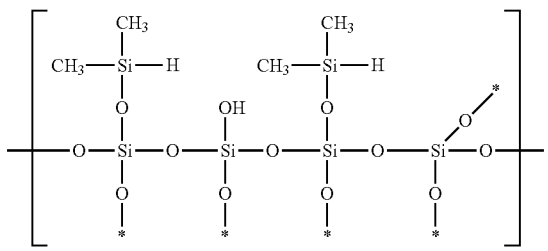

(Bb)

In General Formula (Bb), * means being bonded to at least a Si atom of siloxane.

Examples of the component (B) having a branched structure include HQM-107 (trade name, Hydride Q Resin, manufactured by GELEST, Inc.) and HDP-111 (trade name, polyphenyl-(dimethylhydroxy)siloxane (hydride terminated), RHMe$_2$SiO)(C$_6$H$_5$Si)O]: 99 to 100 mol %, manufactured by GELEST, Inc.).

The component (B) may be used alone or in combination of two or more thereof. In addition, the component (B) having a linear structure and the component (B) having a branched structure may be used in combination.

<Zinc Oxide (Component (C) Surface-Treated with at Least One Surface Treatment Agent of Aminosilane Compound, Mercaptosilane Compound, Isocyanatosilane Compound, Thiocyanatosilane Compound, Aluminum Alkoxide Compound, Zirconium Alkoxide Compound, or Titanium Alkoxide Compound>

The component (C) is zinc oxide surface-treated with at least one surface treatment agent of an aminosilane compound, a mercaptosilane compound, an isocyanatosilane compound, a thiocyanatosilane compound, an aluminum alkoxide compound, a zirconium alkoxide compound, or a titanium alkoxide compound.

The shapes of the zinc oxide constituting the component (C) (hereinafter, simply referred to as "zinc oxide") and the component (C) are not particularly limited and are, for example, indefinite, particulate, or fibrous, preferably particulate.

The average primary particle diameter of zinc oxide used in the present invention is not particularly limited, and is preferably 10 to 300 nm, more preferably 10 to 200 nm, still more preferably 10 to 150 nm, and even still more preferably 10 to 80 nm from the viewpoint of acoustic velocity, adhesiveness, and durability against body fluids of an acoustic lens.

The average primary particle diameter of the component (C) is preferably 10 to 500 nm, more preferably 10 to 200 nm, still more preferably 10 to 100 nm, and most preferably 10 to 50 nm.

The average primary particle diameter is listed in the zinc oxide manufacturer's catalog. In this regard, the average primary particle diameter of zinc oxide for which the average primary particle diameter is not described in the catalog or of zinc oxide newly manufactured can be obtained by averaging the particle diameters measured by transmission electron microscopy (TEM). That is, the shortest diameter and the longest diameter of one zinc oxide in the TEM micrograph are measured, and the arithmetic mean value of the thus measured values is obtained as a particle diameter of one zinc oxide. In the present invention, the particle diameters of 300 randomly selected zinc oxides are averaged and obtained as the average primary particle diameter of zinc oxide.

A commercially available zinc oxide can be used, and examples thereof include FINEX series (trade name, manufactured by Sakai Chemical Industry Co., Ltd.) and ZnO—CX (trade name, manufactured by Sumitomo Osaka Cement Co., Ltd.).

From the viewpoint of acoustic velocity, adhesiveness, and durability against body fluids of an acoustic lens, the surface treatment agent used in the present invention is preferably an aminosilane compound, a mercaptosilane compound, an isocyanatosilane compound, an aluminum alkoxide compound, or a zirconium alkoxide compound; more preferably a mercaptosilane compound, an isocyanatosilane compound, an aluminum alkoxide compound, or a zirconium alkoxide compound; and still more preferably an aluminum alkoxide compound or a zirconium alkoxide compound.

Hereinafter, the surface treatment agent used in the present invention will be specifically described.

(Aminosilane Compound)

The aminosilane compound (silane compound having an amino group) is preferably a silane coupling agent having an amino group. In this regard, the aminosilane compound does not have a Si—N—Si structure. In the aminosilane compound having a Si—N—Si structure (for example, hexamethyldisilazane), an amino group is removed as ammonia in the surface treatment, and therefore the amino group cannot be introduced onto the zinc oxide surface. For this reason, it is difficult to achieve a desired bonding property, and it is also disadvantageous in terms of durability against body fluids.

The aminosilane compound preferably contains at least one compound represented by General Formula (A), and is more preferably a compound represented by General Formula (A).

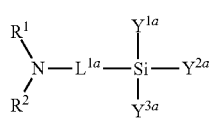

General Formula (A)

In the formula, $R^1$ and $R^2$ represent a hydrogen atom or a substituent. $L^{1a}$ represents a single bond, an alkylene group, an alkenylene group, an alkynylene group, an arylene group, —O—, —S—, —NR$^a$—, an ester bond, a thioester bond, an amide bond, a thioamide bond or a sulfonyl group, or a divalent group consisting of a combination of two or more of these groups or bonds. $R^a$ represents a hydrogen atom or a substituent. $Y^{1a}$ represents a hydroxy group or an alkoxy group. $Y^{2a}$ and $Y^{3a}$ represent a hydroxy group, an alkoxy group, an alkyl group, or a ketoxime group.

Examples of the substituent that can be taken as $R^1$ and $R^2$ include an alkyl group (preferably having 1 to 12 carbon atoms, more preferably 1 to 8 carbon atoms), an alkenyl group (preferably having 2 to 12 carbon atoms, more preferably 2 to 8 carbon atoms), an alkynyl group (preferably having 2 to 12 carbon atoms, more preferably 2 to 8 carbon atoms), and an aryl group (preferably having 6 to 20 carbon atoms, more preferably 6 to 10 carbon atoms). These substituents may further have a substituent, and examples of such a substituent include the above-mentioned substituents mentioned as a substituent that can be taken as $R^1$ and $R^2$ and an amino group.

In addition, $R^1$ and $R^2$ may be combined to represent an alkylidene group (preferably having 2 to 12 carbon atoms, more preferably 2 to 8 carbon atoms).

$L^{1a}$ preferably represents an alkylene group, an alkenylene group, an arylene group, —O—, or —NR$^a$—, more preferably an alkylene group, an arylene group, or —NR$^a$—, and still more preferably an alkylene group.

$Y^{1a}$ preferably represents an alkoxy group.

$Y^{2a}$ and $Y^{3a}$ preferably represent a hydroxy group or an alkoxy group, and more preferably an alkoxy group.

The alkylene group that can be taken as $L^{1a}$ may be linear, branched, or cyclic. The number of carbon atoms in the alkylene group is preferably 1 to 30, more preferably 1 to 25, still more preferably 1 to 20, and even still more preferably 1 to 15. Specific examples of the alkylene group include methylene, ethylene, propylene, tert-butylene, pentylene, cyclohexylene, heptylene, octylene, nonylene, decylene, and undecylene.

The alkenylene group that can be taken as $L^{1a}$ may be linear or branched. The number of carbon atoms in the alkenylene group is preferably 2 to 20, more preferably 2 to 15, still more preferably 2 to 10, and even still more preferably 2 to 6. Specific examples of the alkenylene group include ethenylene and propenylene.

The alkynylene group that can be taken as $L^{1a}$ may be linear or branched. The number of carbon atoms in the alkynylene group is preferably 2 to 20, more preferably 2 to 15, still more preferably 2 to 10, and even still more preferably 2 to 6. Specific examples of the alkynylene group include ethynylene and propynylene.

The number of carbon atoms in the arylene group that can be taken as $L^{1a}$ is preferably 6 to 20, more preferably 6 to 15, still more preferably 6 to 12, and even still more preferably 6 to 10. Specific examples of the arylene group include phenylene and naphthylene.

Examples of the substituent that can be taken as $R^a$ of —NR$^a$— include an alkyl group (preferably having 1 to 12 carbon atoms, more preferably 1 to 8 carbon atoms), an alkenyl group (preferably having 2 to 12 carbon atoms, more preferably 2 to 8 carbon atoms), an alkynyl group (preferably having 2 to 12 carbon atoms, more preferably 2 to 8 carbon atoms), an aryl group (preferably having 6 to 20 carbon atoms, more preferably 6 to 10 carbon atoms), and a heterocyclic group. The heterocyclic ring constituting the heterocyclic group that can be taken as $R^a$ may be a saturated or unsaturated aliphatic heterocyclic ring or aromatic heterocyclic ring, and may be a monocyclic ring or a fused ring. In addition, the heterocyclic ring may also be a bridged ring. Examples of the heteroatom contained in the heterocyclic ring include an oxygen atom, a nitrogen atom, and a sulfur atom. The number of heteroatoms contained in one heterocyclic ring is not particularly limited, and is preferably 1 to 3 and more preferably 1 or 2. The number of carbon atoms in the heterocyclic ring is preferably 2 to 10 and more preferably 4 or 5. The heterocyclic ring is preferably a 3- to 7-membered ring, more preferably a 3- to 6-membered ring, and still more preferably a 3- to 5-membered ring. Specific examples of the heterocyclic ring include an epoxy ring, a 3,4-epoxycyclohexane ring, a furan ring, and a thiophene ring.

Examples of —NR$^a$— include —NH—.

The number of groups or bonds to be combined that constitute a divalent group consisting of a combination of two or more of the above groups or the above bonds that can be taken as $L^{1a}$ (hereinafter, also referred to as "group consisting of a combination that can be taken as $L^{1a}$") is preferably 2 to 8, more preferably 2 to 6, and still more preferably 2 to 4.

In addition, the molecular weight of the group consisting of a combination that can be taken as $L^{1a}$ is preferably 20 to 1,000, more preferably 30 to 500, and still more preferably 40 to 200.

Examples of the group consisting of a combination that can be taken as $L^{1a}$ include a urea bond, a thiourea bond, a carbamate group, a sulfonamide bond, arylene-alkylene, —O-alkylene, amide bond-alkylene, —S-alkylene, alkylene-O-amide bond-alkylene, alkylene-amide bond-alkylene, alkenylene-amide bond-alkylene, alkylene-ester bond-alkylene, arylene-ester bond-alkylene, -(alkylene-O)—, alkylene-O-(alkylene-O)-alkylene (in which "(alkylene-O)" is a repeating unit), arylene-sulfonyl-O-alkylene, and ester bond-alkylene.

The alkyl group constituting the alkoxy group that can be taken as $Y^{1a}$ to $Y^{3a}$ may be linear, branched, or cyclic, and may have a combination of these forms. In the present invention, the alkyl group is preferably a linear alkyl group. The number of carbon atoms in the alkyl group constituting the alkoxy group is preferably 1 to 15, more preferably 1 to 10, still more preferably 1 to 5, and even still more preferably 1 or 2. Specific examples of the alkyl group constituting the alkoxy group include methyl, ethyl, propyl, t-butyl, pentyl, and cyclohexyl.

Examples of the alkyl group that can be taken as $Y^{2a}$ and $Y^{3a}$ include an alkyl group that constitutes the alkoxy group that can be taken as $Y^{1a}$ to $Y^{3a}$, and a preferred form thereof is also the same as the preferred form of the alkyl group that constitutes the alkoxy group that can be taken as $Y^{1a}$ to $Y^{3a}$.

The ketoxime group that can be taken as $Y^{2a}$ and $Y^{3a}$ is a substituent having the following structure.

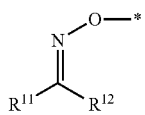

In the above structure, $R^{11}$ and $R^{12}$ represent a substituent, and * represents a bonding site to a silicon atom.

Examples of the substituent that can be taken by and $R^{12}$ include the substituents in $R^a$, and a preferred form thereof is also the same as the preferred form of the substituent that can be taken as $R^a$.

Examples of the ketoxime group include a dimethyl ketoxime group, a methyl ethyl ketoxime group, and a diethyl ketoxime group.

Hereinafter, specific examples of the aminosilane compound used in the present invention will be given, but the present invention is not limited thereto.
3-Aminopropyltrimethoxysilane
3-Aminopropyldimethylmethoxysilane
3-Aminopropylmethyldimethoxysilane
3-Aminopropylmethyldiethoxysilane
3-Aminopropyltriethoxysilane
N-(2-aminoethyl)-3-aminopropylmethyldimethoxysilane
N-(2-aminoethyl)-3-aminopropylmethyldiethoxysilane
N-(2-aminoethyl)-3-aminopropyldimethylmethoxysilane
N-(2-aminoethyl)-3-aminopropyldimethylethoxysilane
N-(2-aminoethyl)-3-aminopropyltrimethoxysilane
N-(2-aminoethyl)-3-aminopropyltriethoxysilane
3-Methyldimethoxysilyl-N-(1,3-dimethyl-butylidene)propylamine
3-Methyldiethoxysilyl-N-(1,3-dimethyl-butylidene)propylamine
3-Trimethoxysilyl-N-(1,3-dimethyl-butylidene)propylamine
3-Triethoxysilyl-N-(1,3-dimethyl-butylidene)propylamine
N-phenyl-3-aminopropylmethyldimethoxysilane
N-phenyl-3-aminopropylmethyldiethoxysilane
N-Phenyl-3-aminopropyltrimethoxysilane
N-Phenyl-3-aminopropyltriethoxysilane
N-(vinylbenzyl)-2-aminoethyl-3-aminopropyltrimethoxysilane (Mercaptosilane Compound)

The mercaptosilane compound (silane compound having a mercapto group (sulfanyl group)) is preferably a silane coupling agent having a mercapto group. The zinc oxide surface-treated with a mercaptosilane compound preferably has a mercapto group derived from the mercaptosilane compound.

The mercaptosilane compound preferably contains at least one compound represented by General Formula (B), and is more preferably a compound represented by General Formula (B).

General Formula (B)

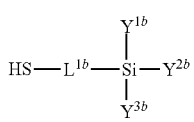

$L^{1b}$, $Y^{1b}$, $Y^{2b}$, and $Y^{3b}$ have the same definition as $L^{1a}$, $Y^{1a}$, $Y_{2a}$, and $Y^{3a}$ of General Formula (A), respectively, and preferred ranges thereof are also the same as in General Formula (A).

Hereinafter, specific examples of the mercaptosilane compound used in the present invention will be given, but the present invention is not limited thereto.
3-Mercaptopropyltrimethoxysilane
3-Mercaptopropyltriethoxysilane
3-Mercaptopropymethyldimethoxysilane
(Mercaptomethyl)methyldiethoxysilane
(Mercaptomethyl)methyldimethoxysilane
(Mercaptomethyl)dimethylethoxysilane
11-Mercaptoundecyltrimethoxysilane (Isocyanatosilane Compound)

The isocyanatosilane compound (preferably a silane compound having an isocyanato group) is preferably a silane coupling agent having an isocyanato group. The zinc oxide surface-treated with an isocyanatosilane compound preferably has an isocyanato group derived from the isocyanatosilane compound.

The isocyanatosilane compound preferably contains at least one compound represented by General Formula (C), and is more preferably a compound represented by General Formula (C).

General Formula (C)

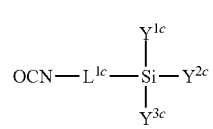

$L^{1c}$, $Y_{1c}$, $Y^{2c}$, and $Y^{3c}$ have the same definition as $L^{1a}$, $Y^{1a}$, $Y^{2a}$, and $Y^{3a}$ of General Formula (A), respectively, and preferred ranges thereof are also the same as in General Formula (A).

In addition, in the present invention, it is also preferable to use a condensate of the compound represented by General Formula (C) and a compound in which the isocyanato group of General Formula (C) is protected by a substituent, as the isocyanatosilane compound. The substituent can be introduced by, for example, an alcohol compound, a phenol compound, an aromatic amine, a lactam, or an oxime. Examples of such an alcohol compound include an alkyl alcohol (preferably having 1 to 12 carbon atoms, more preferably 1 to 8 carbon atoms). In addition, examples of the phenol compound include a phenol and a cresol. In addition, examples of the lactam include an ε-caprolactam.

The "compound in which the isocyanato group of General Formula (C) is protected by a substituent" is a compound in which —NCO of General Formula (C) is substituted with —NHC(=O)OR⁴. $R^4$ represents a substituent, examples of which include an alkyl group (preferably having 1 to 12 carbon atoms, more preferably 1 to 8 carbon atoms).

Hereinafter, specific examples of the isocyanatosilane compound used in the present invention will be given, but the present invention is not limited thereto.
3-Isocyanatopropyltrimethoxysilane
3-Isocyanatopropyltriethoxysilane
Isocyanatomethyltrimethoxysilane
  (The following are isocyanatosilane compounds protected by condensation and substituents)
Tris(3-trimethoxysilylpropyl)isocyanurate
3-(Triethoxysilyl)propyl-t-butyl carbamate
3-(Triethoxysilyl)propylethylcarbamate (Thiocyanatosilane Compound)

The thiocyanatosilane compound (silane compound having a thiocyanato group) is preferably a silane coupling agent having a thiocyanato group. The zinc oxide surface-treated with a thiocyanatosilane compound preferably has a thiocyanato group derived from the thiocyanatosilane compound.

The thiocyanatosilane compound preferably contains at least one compound represented by General Formula (D), and is more preferably a compound represented by General Formula (D).

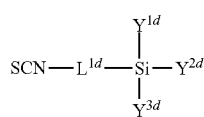

General Formula (D)

$L^{1d}$, $Y^{1d}$, $Y^{2d}$ and $Y^{3d}$ have the same definition as $L_{1a}$, $Y^{1a}$, $Y^{2a}$ and $Y^{3a}$ of General Formula (A), respectively, and preferred ranges thereof are also the same as in General Formula (A).

Hereinafter, specific examples of the thiocyanatosilane compound used in the present invention will be given, but the present invention is not limited thereto.
3-Thiocyanatopropyltrimethoxysilane
3-Thiocyanatopropyltriethoxysilane
Thiocyanatomethyltrimethoxysilane
(Aluminum Alkoxide Compound)

The aluminum alkoxide compound preferably contains an aluminum alkoxide compound containing at least one of an acetonato structure or an acetato structure, and is more preferably an aluminum alkoxide compound containing at least one of an acetonato structure or an acetato structure.

The aluminum alkoxide compound preferably contains at least one compound represented by General Formula (1), is more preferably a compound represented by General Formula (1), and is still more preferably a compound represented by General Formula (1) containing at least one of an acetonato structure or an acetato structure.

General Formula (1):

$R^{1a}$ represents a hydrogen atom, an alkyl group, a cycloalkyl group, an acyl group, an aryl group, or an unsaturated aliphatic group.

The alkyl group that can be taken as $R^{1a}$ includes a linear alkyl group, a branched alkyl group, and an aralkyl group. The number of carbon atoms in the alkyl group is preferably an integer of 1 to 20, more preferably 1 to 15, still more preferably 1 to 10, and particularly preferably 1 to 8, and in a case of an aralkyl group, the number of carbon atoms in the alkyl group is preferably an integer of 7 to 30. Preferred specific examples of the alkyl group include methyl, ethyl, propyl, isopropyl, butyl, sec-butyl, isobutyl, tert-butyl, pentyl, hexyl, heptyl, octyl, decyl, tridecyl, octadecyl, benzyl, and phenethyl.

It is also preferable that the alkyl group that can be taken as $R^{1a}$ has an oxirane ring. The number of ring members of the cycloalkyl group (cycloalkyl group having a structure in which an oxirane ring is condensed) in the epoxycycloalkyl group that can be taken as $R^{1a}$ is preferably 4 to 8, more preferably 5 or 6, and still more preferably 6 (that is, an epoxycyclohexyl group).

In addition, the alkyl group that can be taken as $R^{1a}$ preferably has a group selected from an amino group, an isocyanato group, a mercapto group, an ethylenic unsaturated group, and an acid anhydride group.

The cycloalkyl group that can be taken as $R^{1a}$ preferably has 3 to 20 carbon atoms, more preferably 3 to 15 carbon atoms, still more preferably 3 to 10 carbon atoms, and particularly preferably 3 to 8 carbon atoms. Preferred specific examples of the cycloalkyl group include cyclopropyl, cyclopentyl, and cyclohexyl.

The acyl group that can be taken as $R^{1a}$ preferably has 2 to 40 carbon atoms, more preferably 2 to 30 carbon atoms, still more preferably 2 to 20 carbon atoms, and particularly preferably 2 to 18 carbon atoms.

The aryl group that can be taken as $R^{1a}$ preferably has 6 to 20 carbon atoms, more preferably 6 to 15 carbon atoms, still more preferably 6 to 12 carbon atoms, and particularly preferably 6 to 10 carbon atoms. Preferred specific examples of the aryl group include phenyl and naphthyl, among which phenyl is even still more preferable.

The unsaturated aliphatic group that can be taken as $R^{1a}$ preferably has 1 to 5 carbon-carbon unsaturated bonds, more preferably 1 to 3 carbon-carbon unsaturated bonds, still more preferably 1 or 2 carbon-carbon unsaturated bond, and particularly preferably 1 carbon-carbon unsaturated bond. The unsaturated aliphatic group may contain a heteroatom, and is also preferably a hydrocarbon group. In a case where the unsaturated aliphatic group is a hydrocarbon group, the number of carbon atoms in the group is preferably 2 to 20, more preferably 2 to 15, still more preferably 2 to 10, even still more preferably 2 to 8, and is also preferably 2 to 5. The unsaturated aliphatic group is more preferably an alkenyl group or an alkynyl group.

$R^{1a}$ is preferably a hydrogen atom, an alkyl group, a cycloalkyl group, or an aryl group, and more preferably an alkyl group or a cycloalkyl group.

In a case where the compound of General Formula (1) has two or more $R^{1a}$'s, the two $R^{1a}$'s may be linked to each other to form a ring.

$R^{2a}$ represents a hydrogen atom, an alkyl group, a cycloalkyl group, an acyl group, an alkenyl group, an aryl group, a phosphonate group (phosphonic acid group), or —$SO_2R^{S1}$. $R^{S1}$ represents a substituent.

The alkyl group, cycloalkyl group, acyl group, and aryl group that can be taken as $R^{2a}$ have the same definition as the alkyl group, cycloalkyl group, acyl group, and aryl group that can be taken as $R^{1a}$, respectively, and a preferred form of each group is also the same as in $R^{1a}$. In addition, the alkyl group that can be taken as $R^{2a}$ preferably has an amino group as a substituent.

The alkenyl group that can be taken as $R^{2a}$ includes a linear alkenyl group and a branched alkenyl group. The number of carbon atoms in the alkenyl group is preferably 2 to 18, more preferably 2 to 7, and still more preferably 2 to 5. Preferred specific examples of the alkenyl group include vinyl, allyl, butenyl, pentenyl, and hexenyl. The alkenyl group is preferably a substituted alkenyl group.

The phosphonate group that can be taken as $R^{2a}$ is a group represented by —$P(=O)(-OR^{P1})OR^{P2}$. $R^{P1}$ and $R^{P2}$ represent a hydrogen atom or a substituent, and the substituent is preferably an alkyl group or a phosphonate group. The alkyl group that can be taken as $R^{P1}$ and $R^{P2}$ has the same definition as the alkyl group that can be taken as $R^{1a}$ described above, and a preferred form of the alkyl group is also the same as in $R^{1a}$. The phosphonate group that can be taken as $R^{P1}$ and $R^{P2}$ has the same definition as the phosphonate group that can be taken as $R^{2a}$, and a preferred form thereof is also the same as in $R^{2a}$. In a case where $R^{P1}$ or $R^{P2}$ is a phosphonate group, the $R^{P1}$ and $R^{P2}$ constituting the phosphonate group are each preferably an alkyl group.

As to the phosphonate group that can be taken as $R^{2a}$, it is preferable that both $R^{P1}$ and $R^{P2}$ are alkyl groups, or $R^{P1}$ is a hydrogen atom and $R^{P2}$ is a phosphonate group.

Since the phosphonate group is tautomeric with a phosphite group (phosphorous acid group), the phosphonate group in the present invention means to include the phosphite group.

In —$SO_2R^{S1}$ that can be taken as $R^{2a}$, the substituent $R^{S1}$ is preferably an alkyl group or an aryl group. Preferred forms of the alkyl group and aryl group that can be taken as $R^{S1}$ include the above-mentioned preferred forms of the alkyl group and aryl group that can be taken as $R^{1a}$, respectively. Above all, phenyl having an alkyl group as a substituent is preferable for $R^{S1}$. The preferred form of the alkyl group is the same as the above-mentioned preferred form of the alkyl group that can be taken as $R^{1a}$.

In a case where the compound represented by General Formula (1) has two or more $R^{2a}$'s, the two $R^{2a}$'s may be linked to each other to form a ring.

m1 is an integer of 0 to 2.

In General Formula (1), it is preferable that at least one of $OR^{2a}$'s has an acetonato structure. The acetonato structure means a structure in which one hydrogen ion is removed from acetone or a compound having a structure in which acetone has a substituent and which is coordinated to Al. The coordinating atom coordinated to the Al is usually an oxygen atom. The acetonato structure is preferably a structure in which an acetylacetone structure ("$CH_3$—C(=O)—$CH_2$—C(=O)—$CH_3$") is taken as a basic structure, one hydrogen ion is removed from the structure, and the structure is coordinated to Al through an oxygen atom as a coordinating atom (that is, an acetylacetonato structure). The phrase "an acetylacetone structure is taken as a basic structure" means to include, in addition to the acetylacetone structure, a structure in which a hydrogen atom of the acetylacetone structure is substituted with a substituent. Examples of the form in which $OR^{2a}$ has an acetonato structure include compounds SL-2 and SL-3, which will be described later.

In General Formula (1), it is preferable that at least one of $OR^{2a}$'s has an acetato structure. In the present invention, the acetato structure means a structure in which one hydrogen ion is removed from acetic acid or an acetic acid ester, or a compound having a structure in which the acetic acid or acetic acid ester has a substituent (including a form in which the methyl group of acetic acid has an alkyl group as a substituent), and which is coordinated to Al. The coordinating atom coordinated to the Al is usually an oxygen atom. The acetato structure is preferably a structure in which an alkylacetoacetato structure ("$CH_3$—C(=O)—$CH_2$—C(=O)—O—$R_{alk}$") (where $R_{alk}$ represents an alkyl group (which is preferably an alkyl group having 1 to 10 carbon atoms, and more preferably an alkyl group having 1 to 4 carbon atoms)) is taken as a basic structure, one hydrogen ion is removed from the structure, and the structure is coordinated to Al through an oxygen atom as a coordinating atom (that is, an alkylacetoacetato structure). The phrase "an alkylacetoacetato structure is taken as a basic structure" means to include, in addition to the alkylacetoacetato structure, a structure in which a hydrogen atom of the alkylacetoacetato structure is substituted with a substituent. Examples of the form in which $OR^{2a}$ has an acetato structure include compounds SL-3, SL-4, and SL-5, which will be described later.

The group that can be taken as $R^{1a}$ or $R^{2a}$ may have an anionic group having a counter cation (salt-type substituent) as a substituent. The anionic group means a group capable of forming an anion. Examples of the anionic group having a counter cation include a carboxylic acid ion group having an ammonium ion as a counter cation. In this case, the counter cation may be present in the compound represented by General Formula (1) such that the charge of the entire compound becomes zero. This also applies to the compound represented by General Formula (2) and the compound represented by General Formula (3), which will be described later.

Hereinafter, specific examples of the aluminum alkoxide compound used in the present invention will be given, but the present invention is not limited thereto.

Aluminum triethylate
Aluminum triisopropylate
Aluminum tri-sec-butyrate
Aluminum tris(ethylacetoacetate)
Ethyl acetoacetate aluminum diisopropylate
Aluminum monoacetylacetonate bis(ethylacetoacetate)
Aluminum tris(acetylacetonate)
Diisopropoxy aluminum-9-octadecenylacetoacetate
Aluminum diisopropoxy monoethylacetoacetate
Mono sec-butoxyaluminum diisopropylate
Diethylacetoacetate aluminum isopropylate
Aluminum bisethylacetoacetate monoacetylacetonate
Aluminum octadecylacetoacetate diisopropylate (Zirconium Alkoxide Compound)

The zirconium alkoxide compound preferably contains a zirconium alkoxide compound containing at least one of an acetonato structure, an acetato structure, or a lactato structure, more preferably contains a zirconium alkoxide compound containing at least one of an acetonato structure or an acetato structure, and is still more preferably a zirconium alkoxide compound containing at least one of an acetonato structure or an acetato structure.

The zirconium alkoxide compound preferably contains at least one compound represented by General Formula (2), is more preferably a compound represented by General Formula (2), and is still more preferably a compound represented by General Formula (2) containing at least one of an acetonato structure or an acetato structure.

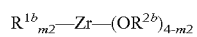

General Formula (2):

$R^{1b}$ represents a hydrogen atom, an alkyl group, a cycloalkyl group, an acyl group, an aryl group, or an unsaturated aliphatic group.

As the alkyl group, the cycloalkyl group, the acyl group, the aryl group, and the unsaturated aliphatic group, for example, an alkyl group, a cycloalkyl group, an acyl group, an aryl group, and an unsaturated aliphatic group that can be taken as $R^{1a}$ of General Formula (1) can be adopted.

$R^{2b}$ represents a hydrogen atom, an alkyl group, a cycloalkyl group, an acyl group, an alkenyl group, an aryl group, a phosphonate group, or —$SO_2R^{S2}$. $R^{S2}$ represents a substituent.

As the alkyl group, the cycloalkyl group, the acyl group, the alkenyl group, the aryl group, and the phosphonate group, for example, an alkyl group, a cycloalkyl group, an acyl group, an alkenyl group, an aryl group, and a phosphonate group that can be taken as $R^{2a}$ of General Formula (1) can be adopted. In addition, as the substituent that can be taken as $R^{S2}$, for example, a substituent that can be taken as $R^{S1}$ of General Formula (1) can be adopted.

m2 is an integer of 0 to 3.

In General Formula (2), it is preferable that at least one of $OR^{2b}$'s has an acetonato structure. The acetonato structure has the same definition as the acetonato structure described by General Formula (1). Examples of the form in which $OR^{2b}$ has an acetonato structure include compounds SZ-3 and SZ-6, which will be described later.

In addition, in General Formula (2), it is preferable that at least one of $OR^{2b}$'s has an acetato structure. The acetato structure has the same definition as the acetato structure described by General Formula (1). Examples of the form in which $OR^{2b}$ has an acetato structure include compounds SZ-5 and SZ-7, which will be described later. The compound SZ-5 corresponds to the form in which $R^{2b}$ is an acyl group in General Formula (1).

In addition, in General Formula (2), it is preferable that at least one of $OR^{2b}$'s has a lactato structure. The lactato structure means a structure in which a lactic acid ion (lactate) is taken as a basic structure, and one hydrogen ion is removed from the basic structure and which is coordinated to Zr. The phrase "a lactic acid ion is taken as a basic structure" means to include, in addition to the lactic acid ion, a structure in which a hydrogen atom of the lactic acid ion is substituted with a substituent. The coordinating atom coordinated to the Zr is usually an oxygen atom. Examples of the form in which $OR^{2b}$ has a lactato structure include a compound SZ-4 which will be described later.

Hereinafter, specific examples of the zirconium alkoxide compound used in the present invention will be given, but the present invention is not limited thereto.

Tetrapropoxyzirconium (also known as zirconium tetra-n-propoxide)
Tetrabutoxyzirconium (also known as zirconium tetra-n-butoxide)
Zirconium tetraacetylacetonate
Zirconium tributoxy monoacetylacetonate
Zirconium dibutoxy bis(acetyl acetonate)
Zirconium dibutoxy bis(ethyl acetoacetate)
Zirconium tributoxyethylacetoacetate
Zirconium monobutoxyacetylacetonate bis(ethyl acetoacetate)
Zirconium tributoxy monostearate (also known as zirconium stearate tri-n-butoxide)
Zirconium stearate
Zirconium lactate ammonium salt
Zirconium monoacetylacetonate (Titanium Alkoxide Compound)

The titanium alkoxide compound preferably contains a titanium alkoxide compound containing at least one atom of N, P, or S, and is more preferably a titanium alkoxide compound containing at least one atom of N, P, or S. In addition, it is also preferable that the titanium alkoxide compound has an acetato structure.

The titanium alkoxide compound preferably contains at least one compound represented by General Formula (3), is more preferably a compound represented by General Formula (3), and is still more preferably a compound represented by General Formula (3) containing at least one atom of N, P, or S.

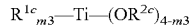  General Formula (3):

$R^{1c}$ represents a hydrogen atom, an alkyl group, a cycloalkyl group, an acyl group, an aryl group, or an unsaturated aliphatic group.

As the alkyl group, the cycloalkyl group, the acyl group, the aryl group, and the unsaturated aliphatic group, for example, an alkyl group, a cycloalkyl group, an acyl group, an aryl group, and an unsaturated aliphatic group that can be taken as $R^{1a}$ of General Formula (1) can be adopted.

$R^{2c}$ represents a hydrogen atom, an alkyl group, a cycloalkyl group, an acyl group, an alkenyl group, an aryl group, a phosphonate group, or $-SO_2R^{s3}$. $R^{s3}$ represents a substituent.

As the alkyl group, the cycloalkyl group, the acyl group, the alkenyl group, the aryl group, and the phosphonate group, for example, an alkyl group, a cycloalkyl group, an acyl group, an alkenyl group, an aryl group, and a phosphonate group that can be taken as $R^{ea}$ of General Formula (1) can be adopted. In addition, as the substituent that can be taken as $R^{s3}$, for example, a substituent that can be taken as $R^{s1}$ of General Formula (1) can be adopted.

m3 is an integer of 0 to 3.

The compound represented by General Formula (3) preferably contains at least one atom of N, P, or S. In a case where the compound represented by General Formula (3) has N, it is preferable to have the N as an amino group.

In a case where the compound represented by General Formula (3) has P, it is preferable to have the P as a phosphate group (phosphoric acid group) or a phosphonate group (phosphonic acid group).

In a case where the compound represented by General Formula (3) has S, it is preferable to have the S as a sulfonyl group ($-SO_2-$).

In addition, it is also preferable that the compound represented by General Formula (3) has an acyl group as $R^{2c}$, that is, has the above-mentioned acetato structure as $OR^{2c}$.

Hereinafter, specific examples of the titanium alkoxide compound used in the present invention will be given, but the present invention is not limited thereto.

Isopropyltriisostearoyl titanate
Isopropyltridodecylbenzenesulfonyl titanate
Isopropyltrioctanoyl titanate
Isopropyltri(dioctylphosphite)titanate
Isopropyltris(dioctylpyrophosphate)titanate
Isopropyltri(dioctylsulfate)titanate
Isopropyltricumylphenyl titanate
Isopropyltri(N-aminoethyl-aminoethyl)titanate
Isopropyldimethacryl isostearoyl titanate
Isopropylisostearoyl diacryl titanate
Isobutyltrimethyl titanate
Diisostearoylethylene titanate
Diisopropyl bis(dioctylpyrophosphate)titanate
Dioctyl bis(ditridecylphosphate)titanate
Dicumyl phenyl oxyacetate titanate
Bis(dioctylpyrophosphate)oxyacetate titanate
Bis(dioctylpyrophosphate)ethylene titanate
Tetraisopropyl titanate
Tetrabutyl titanate
Tetraoctyl titanate
Tetrastearyl titanate
Tetraisopropyl bis(dioctylphosphite)titanate
Tetraoctyl bis(di-tridecylphosphite)titanate
Tetra(2,2-diallyloxymethyl-1-butyl)bis(di-tridecyl)phosphite titanate
Butyl titanate dimer
Titanium tetraacetylacetonate
Titanium ethyl acetoacetate
Titanium octylene glycolate
Titanium di-2-ethylhexoxybis(2-ethyl-3-hydroxyhexoxide)

The mass ratio of zinc oxide to the surface treatment agent in the component (C) is not particularly limited, and for example, the surface treatment agent is preferably 5 to 100 parts by mass, more preferably 10 to 80 parts by mass, and still more preferably 10 to 50 parts by mass with respect to 100 parts by mass of zinc oxide, and from the viewpoint of adhesiveness and durability against body fluids of an acoustic lens, the surface treatment agent is even still more preferably 20 to 50 parts by mass and most preferably 20 to 40 parts by mass.

The mass ratio of zinc oxide to the surface treatment agent in the component (C) has the same meaning as the mass ratio of the amount of zinc oxide to the amount of the surface treatment agent used in the surface treatment. The mass ratio of zinc oxide to the surface treatment agent in the component (C) can be calculated from the mass of zinc oxide and the mass of the component (C) with a thermogravimetric analysis (TGA) or the like by heating the component (C) to 500° C. or higher to remove an organic component to obtain an inorganic component (zinc oxide).

A surface treatment agent other than the above-mentioned surface treatment agent may be used as long as the effect of the present invention is not impaired.

The surface treatment can be carried out by a conventional method.

As for the component (C), it is not necessary that the entire surface of zinc oxide is treated with a surface treatment agent. For example, preferably 50% or more, more preferably 70% or more, and still more preferably 90% or more of 100% surface area of zinc oxide is surface-treated.

The component (C) may be used alone or in combination of two or more thereof.

Of a total of 100 parts by mass of each content of the components (A) to (C), the content of the component (C) is preferably 1 to 100 parts by mass, more preferably 20 to 80 parts by mass, still more preferably 30 to 70 parts by mass, and even still more preferably 40 to 60 parts by mass, from the viewpoint of acoustic velocity, adhesiveness, and durability against body fluids of an acoustic lens.

In addition, the content of each of the components (A) to (C) in the total of 100 parts by mass of each content of the components (A) to (C) is preferably in the following range.

The content of the component (A) is preferably 20 to 80 parts by mass, more preferably 30 to 65 parts by mass, and still more preferably 35 to 55 parts by mass.

The content of the component (B) is preferably 0.1 to 20 parts by mass, more preferably 0.2 to 10 parts by mass, still more preferably 0.3 to 5 parts by mass, and most preferably 0.3 to 1.5 parts by mass.

<Other Components>

In addition to the components (A) to (C), at least one of a catalyst for an addition polymerization reaction, a curing retarder, a solvent, a dispersant, a pigment, a dye, an antistatic agent, an antioxidant, a flame retardant, or a thermal conductivity improver can be appropriately formulated in the composition for an acoustic lens according to the embodiment of the present invention.

—Catalyst—

The catalyst may be, for example, platinum or a platinum-containing compound (hereinafter, also simply referred to as a platinum compound). An ordinary platinum or platinum compound can be used as the platinum or platinum compound.

Specific examples of the platinum or platinum compound include platinum black or platinum supported on an inorganic compound or carbon black, chloroplatinic acid or an alcohol solution of chloroplatinic acid, a complex salt of chloroplatinic acid and olefin, and a complex salt of chloroplatinic acid and vinyl siloxane. The catalyst may be used alone or in combination of two or more thereof.

The catalyst is preferably used in a hydrosilylation reaction (addition curing reaction) in which the Si—H group of the component (B) is added to the vinyl group of the component (A).

Here, the catalyst may be contained in the composition for an acoustic lens according to the embodiment of the present invention, or may be brought into contact with the composition for an acoustic lens without being contained in the composition for an acoustic lens.

Examples of commercially available platinum catalysts include platinum compounds (trade name: PLATINUM CYCLOVINYLMETHYLSILOXANE COMPLEX IN CYCLIC METHYLVINYLSILOXANES (SIP6832.2), Pt concentration: 2% by mass, and trade name: PLATINUM DIVINYLTETRAMETHYLDISILOXANE COMPLEX IN VINYL-TERMINATED POLYDIMETHYLSILOXANE (SIP6830.3), Pt concentration: 3% by mass, both manufactured by Gelest, Inc.).

In a case where the catalyst is contained in the composition for an acoustic lens according to the embodiment of the present invention, the content of the catalyst is not particularly limited. From the viewpoint of reactivity, the content of the catalyst is preferably 0.00001 to 0.05 parts by mass, more preferably 0.00001 to 0.01 parts by mass, still more preferably 0.00002 to 0.01 parts by mass, and particularly preferably 0.00005 to 0.005 parts by mass, with respect to a total of 100 parts by mass of the components (A) to (C).

In addition, the curing temperature can be adjusted by selecting an appropriate platinum catalyst. For example, platinum-vinyl disiloxane is used for room temperature curing (RTV) at 50° C. or lower, and platinum-cyclic vinyl siloxane is used for high temperature curing (HTV) at 130° C. or higher.

—Curing Retarder—

In the present invention, a curing retarder for the curing reaction can be appropriately used. The curing retarder is used for the purpose of delaying the addition curing reaction, and examples thereof include a low molecular weight vinyl methylsiloxane homopolymer (trade name: VMS-005, manufactured by Gelest, Inc.).

The curing rate, that is, the working time can be adjusted depending on the content of the curing retarder.

[Viscosity of Composition for Acoustic Lens Before Curing]

The viscosity of the composition for an acoustic lens before the curing reaction is preferably low from the viewpoint of uniformly dispersing the components (A) to (C). The viscosity of the composition for an acoustic lens before adding a catalyst for initiating the curing reaction is measured, from the viewpoint of measuring the viscosity before curing. Specifically, the viscosity of the composition for an acoustic lens can be measured by the method described in WO2017/130890A.

The viscosity (23° C.) is preferably 5,000 Pa·s or less, more preferably 1,000 Pa·s or less, and particularly preferably 200 Pa·s or less. The practical lower limit of the viscosity is 10 Pa·s or more.

<Method for Manufacturing Composition for Acoustic Lens, Acoustic Lens, and Acoustic Wave Probe>

The composition for an acoustic lens according to the embodiment of the present invention can be prepared by a conventional method.

The composition for an acoustic lens according to the embodiment of the present invention can be obtained, for example, by kneading the components constituting the composition for an acoustic lens using a kneader, a pressurized kneader, a Banbury mixer (continuous kneader), a two-roll kneading device, or the like. The mixing order of each component is not particularly limited.

From the viewpoint of obtaining a uniform composition, it is preferable to first prepare a polysiloxane mixture in which the component (C) is dispersed in the components (A) and (B). Then, a composition for an acoustic lens can be produced by adding a catalyst to the polysiloxane mixture in which the component (C) is dispersed, followed by defoaming under reduced pressure.

The conditions for kneading the polyorganosiloxane mixture in which the component (C) is dispersed are not particularly limited as long as the component (C) is dispersed. For example, it is preferable to knead the polyorganosiloxane mixture at 10° C. to 50° C. for 1 to 72 hours.

A silicone resin can be obtained by curing the composition for an acoustic lens according to the embodiment of the present invention thus obtained. Specifically, for example, a silicone resin can be obtained by heat-curing the composition for an acoustic lens at 20° C. to 200° C. for 5 to 500 minutes. The shape of the silicone resin is not particularly limited. For example, the silicone resin may be formed into a preferable shape as an acoustic lens by a mold at the time of curing, or may be used as a desired acoustic lens by obtaining a sheet-like silicone resin and cutting the resin.

The composition for an acoustic lens according to the embodiment of the present invention is useful for medical members, and can be preferably used, for example, in an acoustic wave probe and an acoustic wave measurement apparatus. The acoustic wave measurement apparatus according to the embodiment of the present invention is not limited to an ultrasound diagnostic apparatus or a photoacoustic wave measurement apparatus, but refers to a device that receives an acoustic wave reflected or generated by an object and displays the received acoustic wave as an image or a signal intensity.

In particular, the composition for an acoustic lens according to the embodiment of the present invention can be suitably used as a material for an acoustic lens of a probe for an ultrasound diagnostic apparatus, a material for an acoustic lens in a photoacoustic wave measurement apparatus or an ultrasonic endoscope, and a material for an acoustic lens in an ultrasound probe equipped with a capacitive micromachined ultrasonic transducer (cMUT) as an ultrasonic transducer array.

Specifically, the acoustic lens according to the embodiment of the present invention is preferably applied to an acoustic wave measurement apparatus such as the ultrasound diagnostic apparatus described in JP2003-169802A and the like, or the photoacoustic wave measurement apparatus described in JP2013-202050A, JP2013-188465A, and the like.

The acoustic wave probe according to the embodiment of the present invention can be manufactured by a conventional method, except that an acoustic lens is formed of the composition for an acoustic lens according to the embodiment of the present invention.

<<Acoustic Wave Probe>>

The configuration of the acoustic wave probe according to the embodiment of the present invention will be described in more detail below based on the configuration of the ultrasound probe in the ultrasound diagnostic apparatus described in FIG. 1. The ultrasound probe is a probe which particularly uses an ultrasonic wave as an acoustic wave in an acoustic wave probe. For this reason, a basic structure of the ultrasound probe can be applied to the acoustic wave probe as it is.

—Ultrasound Probe—

An ultrasound probe 10 is a main component of the ultrasound diagnostic apparatus and has a function of generating an ultrasonic wave and transmitting and receiving an ultrasonic beam. The configuration of the ultrasound probe 10 is provided in the order of an acoustic lens 1, an acoustic matching layer 2, a piezoelectric element layer 3, and a backing material 4 from a distal end portion (the surface coming into contact with a living body which is a test object) as shown in FIG. 1. In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

<Piezoelectric Element Layer>

The piezoelectric element layer 3 is a portion which generates an ultrasonic wave and in which an electrode is attached to both sides of a piezoelectric element. In a case where voltage is applied to the electrode, the piezoelectric element layer generates an ultrasonic wave through repeated contraction and expansion of the piezoelectric element and through vibration.

A so-called ceramics inorganic piezoelectric body obtained by a polarization treatment of quartz crystals, single crystals such as $LiNbO_3$, $LiTaO_3$, and $KNbO_3$, thin films of ZnO and AlN, $Pb(Zr,Ti)O_3$-based sintered body, and the like is widely used as the material constituting a piezoelectric element. In general, piezoelectric ceramics such as lead zirconate titanate (PZT) with good conversion efficiency are used.

In addition, sensitivity having a wider band width is required for a piezoelectric element detecting a reception wave on a high frequency side. For this reason, an organic piezoelectric body has been used in which an organic polymer material such as polyvinylidene fluoride (PVDF) is used as the piezoelectric element being suitable for a high frequency or a wide band.

Furthermore, cMUT using micro electro mechanical systems (MEMS) technology in which an array structure, which shows excellent short pulse characteristics, excellent wideband characteristics, and excellent mass productivity and has less characteristic variations, is obtained is disclosed in JP2011-071842A or the like.

In the present invention, it is possible to preferably use any piezoelectric element material.

<Backing Material>

The backing material 4 is provided on a rear surface of the piezoelectric element layer 3 and contributes to the improvement in distance resolution in an ultrasound diagnostic image by shortening the pulse width of an ultrasonic wave through the suppression of excess vibration.

<Acoustic Matching Layer>

The acoustic matching layer 2 is provided in order to reduce the difference in acoustic impedance between the piezoelectric element layer 3 and a test object and to efficiently transmit and receive an ultrasonic wave.

<Acoustic Lens>

The acoustic lens 1 is provided to focus an ultrasonic wave in a slice direction by utilizing refraction to improve the resolution. In addition, it is necessary for the acoustic lens to achieve matching of an ultrasonic wave with acoustic impedance (1.4 to 1.7 Mrayl in a case of a human body) of a living body which is a test object after being closely attached to the living body.

That is, sensitivity of transmission and reception of an ultrasonic wave is improved using a material of which the acoustic velocity is sufficiently lower than that of a human body, and the acoustic impedance is close to a value of the skin of a human body, as the material of the acoustic lens 1.

The composition for an acoustic lens according to the embodiment of the present invention can be preferably used as an acoustic lens material.

The operation of the ultrasound probe 10 having such a configuration will be described. The piezoelectric element layer 3 is resonated after applying a voltage to the electrodes provided on both sides of the piezoelectric element layer 3, and an ultrasonic signal is transmitted to a test object from the acoustic lens 1. During reception of the ultrasonic signal, the piezoelectric element layer 3 is vibrated using the signal (echo signal) reflected from the test object and this vibration is electrically converted into a signal to obtain an image.

In particular, it is possible to confirm for the acoustic lens obtained from the composition for an acoustic lens according to the embodiment of the present invention to have a significant sensitivity improving effect at a transmission frequency of an ultrasonic wave of about 10 MHz or higher as a general medical ultrasonic transducer. A particularly significant sensitivity improving effect can be expected particularly at a transmission frequency of an ultrasonic wave of 15 MHz or higher.

Hereinafter, a device in which the acoustic lens obtained from the composition for an acoustic lens according to the embodiment of the present invention exerts a particular function with respect to the problems of the related art will be described in detail.

The composition for an acoustic lens according to the embodiment of the present invention also exhibits excellent effects on devices other than those described below.

—Ultrasound Probe Equipped with Capacitive Micromachined Ultrasonic Transducer (cMUT)—

In a case where the cMUT device described in JP2006-157320A, JP2011-71842A, or the like is used in an ultrasonic transducer array, its sensitivity is generally lower than that of a transducer using general piezoelectric ceramics (PZT).

However, using the acoustic lens obtained from the composition for an acoustic lens according to the embodiment of the present invention makes it possible to compensate for the lack of sensitivity of cMUT. This makes it possible to bring the sensitivity of the cMUT closer to the performance of a transducer of the related art.

Since the cMUT device is produced by MEMS technology, it is possible to provide the market with an ultrasound probe having higher mass productivity and lower cost than a piezoelectric ceramic probe.

—Photoacoustic Wave Measurement Apparatus Using Photoacoustic Imaging—

Photoacoustic imaging (PAI) described in JP2013-158435A or the like displays an image or a signal intensity of an ultrasonic wave generated in a case where the inside of a human body is irradiated with light (an electromagnetic wave), and the human tissue adiabatically expands due to the irradiated light.

—Ultrasonic Endoscope—

Since the signal line cable of the ultrasonic endoscope described in JP2008-311700A or the like is longer than that of a transducer for the body surface due to its structure, it is a problem to improve the sensitivity of the transducer due to the cable loss of an ultrasonic wave. In addition, it is said that there is no effective means for improving sensitivity for this problem for the following reasons.

First, in a case where it is an ultrasound diagnostic apparatus for the body surface, an amplifier circuit, an AD conversion IC, or the like can be installed at the tip of a transducer. On the other hand, since an ultrasonic endoscope is used by insertion thereof into the body, an installation space of a transducer is narrow, and it is difficult to install an amplifier circuit, an AD conversion IC, or the like at the tip of the transducer.

Secondly, a piezoelectric single crystal used in a transducer in an ultrasound diagnostic apparatus for the body surface is difficult to apply to a transducer with a transmission frequency of an ultrasonic wave of 10 to 15 MHz or higher due to its physical characteristics and process suitability. Meanwhile, since an ultrasonic wave for an endoscope is generally a probe having a transmission frequency of an ultrasonic wave of 10 to 15 MHz or higher, it is difficult to improve the sensitivity by using a piezoelectric single crystal material.

However, using the acoustic lens obtained from the composition for an acoustic lens according to the embodiment of the present invention makes it possible to improve the sensitivity of an ultrasonic transducer for an endoscope.

In addition, even in a case where the same transmission frequency of an ultrasonic wave (for example, 15 MHz) is used, it is particularly effective in a case where the acoustic lens obtained from the composition for an acoustic lens according to the embodiment of the present invention is used in an ultrasonic transducer for an endoscope.

EXAMPLES

The present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like.

[Preparation Example] Preparation Example of Surface-Treated Zinc Oxide (C-1)

3.0 parts by mass of 3-aminopropyltrimethoxysilane, 100 parts by mass of methanol, and 3.3 parts by mass of distilled water were mixed and then allowed to stand at 23° C. for 1 hour to proceed with the hydrolysis of the methoxy group. 10.0 parts by mass of zinc oxide (trade name "FINEX-30", manufactured by Sakai Chemical Industry Co., Ltd., average primary particle diameter: 35 nm) were added to this solution. Using a homogenizer ("EXCEL AUTO HOMOGENIZER ED-7" (trade name), manufactured by Nippon Seiki Co., Ltd.), the mixture was stirred at a rotation speed of 10,000 rpm for 60 minutes while cooling such that the liquid temperature did not exceed 50° C., and a surface treatment was carried out while pulverizing.

The mixture after stirring and pulverizing above was filtered off, and the obtained solid was heated and dried at 100° C. for 30 minutes to obtain powdery surface-treated zinc oxide particles (C-1) (component (C)).

Surface-treated zinc oxides (C-2) to (C-29) were prepared in the same manner as the surface-treated zinc oxide (C-1), except that, in the preparation of the surface-treated zinc oxide (C-1), the raw materials were used in the compositions shown in Table 1 below.

TABLE 1

|  |  | C-1 | C-2 | C-3 | C-4 | C-5 | C-6 | C-7 | C-8 | C-9 | C-10 |
|---|---|---|---|---|---|---|---|---|---|---|---|
| Zinc Oxide (Q) | Type | Q-1 | Q-1 | Q-1 | Q-1 | Q-1 | Q-1 | Q-1 | Q-1 | Q-1 | Q-1 |
|  | Average primary particle diameter [nm] | 35 | 35 | 35 | 35 | 35 | 35 | 35 | 35 | 35 | 35 |
| Surface treatment agent (S) | Type | SA-1 | SA-2 | SM-1 | SM-2 | SI-1 | SI-2 | ST-1 | ST-2 | ST-3 | SL-1 |
|  | Number of acetonato structure | — | — | — | — | — | — | — | — | — | — |
|  | Number of acetato structure | — | — | — | — | — | — | — | — | — | — |
|  | Amount used [parts by mass] | 30 | 30 | 30 | 30 | 30 | 30 | 30 | 30 | 30 | 30 |

|  |  | C-11 | C-12 | C-13 | C-14 | C-15 | C-16 | C-17 | C-18 | C-19 | C-20 |
|---|---|---|---|---|---|---|---|---|---|---|---|
| Zinc Oxide (Q) | Type | Q-1 | Q-1 | Q-1 | Q-1 | Q-1 | Q-1 | Q-1 | Q-1 | Q-1 | Q-1 |
|  | Average primary particle diameter [nm] | 35 | 35 | 35 | 35 | 35 | 35 | 35 | 35 | 35 | 35 |
| Surface treatment agent (S) | Type | SL-2 | SL-3 | SL-4 | SL-5 | SZ-1 | SZ-2 | SZ-3 | SZ-4 | SZ-5 | SZ-6 |
|  | Number of acetonato structure | 3 | 1 | — | — | — | — | 4 | — | — | 1 |
|  | Number of acetato structure | — | 2 | 3 | 1 | — | — | — | — | — | — |
|  | Amount used [parts by mass] | 30 | 30 | 30 | 30 | 30 | 30 | 30 | 30 | 30 | 30 |

|  |  | C-21 | C-22 | C-23 | C-24 | C-25 | C-26 | C-27 | C-28 | C-29 |
|---|---|---|---|---|---|---|---|---|---|---|
| Zinc Oxide (Q) | Type | Q-1 | Q-2 | Q-3 | Q-4 | Q-1 | Q-1 | Q-1 | Q-1 | Q-1 |
|  | Average primary particle diameter [nm] | 35 | 20 | 60 | 250 | 35 | 35 | 35 | 35 | 35 |
| Surface treatment agent (S) | Type | SZ-7 | SL-4 | SL-4 | SL-4 | SL-4 | SL-4 | SC-1 | SC-2 | SC-3 |
|  | Number of acetonato structure | — | — | — | — | — | — | — | — | — |
|  | Number of acetato structure | 2 | — | — | — | — | — | — | — | — |
|  | Amount used [parts by mass] | 30 | 30 | 30 | 30 | 10 | 50 | 30 | 30 | 30 |

<Notes of tables>

[Zinc oxide (Q)]

Q-1: untreated zinc oxide (trade name "FINEX-30", manufactured by Sakai Chemical Industry Co., Ltd., average primary particle diameter: 35 nm)

Q-2: untreated zinc oxide (trade name "FINEX-50", manufactured by Sakai Chemical Industry Co., Ltd., average primary particle diameter: 20 nm)

Q-3: untreated zinc oxide (trade name "FINEX-25", manufactured by Sakai Chemical Industry Co., Ltd., average primary particle diameter: 60 nm)

Q-4: untreated zinc oxide (trade name "ZnO-CX", manufactured by Sumitomo Osaka Cement Co., Ltd., average primary particle diameter: 250 nm)

[Surface Treatment Agent (S)]

<Aminosilane Compound>

(SA-1):
3-Aminopropyltrimethoxysilane (trade name "SIA0611.0", manufactured by Gelest, Inc.)

<Mercaptosilane Compound>

(SM-1):
3-Mercaptopropyltrimethoxysilane (trade name "SIM6476.0", manufactured by Gelest, Inc.)

(SM-2):
11-Mercaptoundecyltrimethoxysilane (trade name "SIM6480.0", manufactured by Gelest, Inc.)

<Isocyanatosilane Compound>

(SI-1):
3-Isocyanatopropyltrimethoxysilane (trade name "SI6456.0", manufactured by Gelest, Inc.)

(SI-2):
Isocyanatomethyltrimethoxysilane (trade name "SI6453.8", manufactured by Gelest, Inc.)

<Titanium Alkoxide Compound>

(ST-1):
Isopropyltriisostearoyl titanate (trade name "PLENACT TTS", manufactured by Ajinomoto Fine-Techno Co., Inc.)

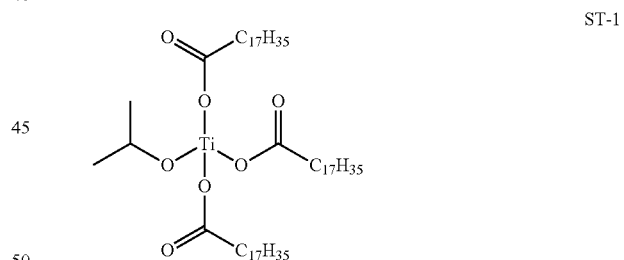

(ST-2):
Dioctyl bis(ditridecylphosphate)titanate ("PLENACT 46B", Ajinomoto Fine-Techno Co., Inc.)

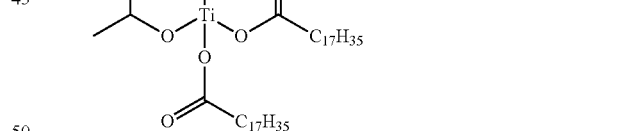

(ST-3):

Isopropyl tri(N-aminoethyl-aminoethyl)titanate (trade name "PLENACT 44", manufactured by Ajinomoto Fine-Techno Co., Inc.)

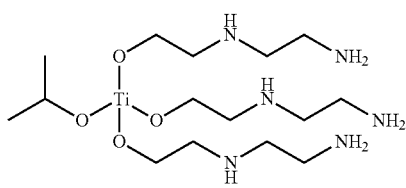

ST-3

<Aluminum Alkoxide Compound>

(SL-1):

Aluminum tri-sec-butyrate (trade name "ASBD", manufactured by Kawaken Fine Chemicals Co., Ltd.)

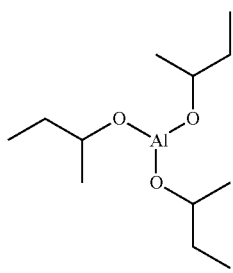

SL-1

(SL-2):

Aluminum trisacetylacetonate (trade name "ORGATIX AL-3100", manufactured by Matsumoto Fine Chemical Co., Ltd.)

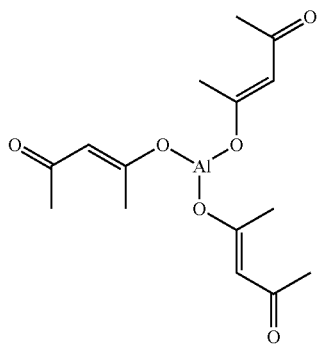

SL-2

(SL-3):

Aluminum bisethylacetoacetate monoacetylacetonate (trade name "ORGATIX AL-3200", manufactured by Matsumoto Fine Chemical Co., Ltd.)

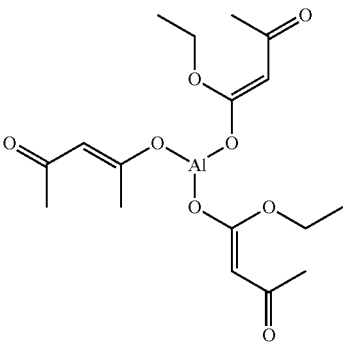

SL-3

(SL-4):

Aluminum trisethylacetoacetate (trade name "ORGATIX AL-3215", manufactured by Matsumoto Fine Chemical Co., Ltd.)

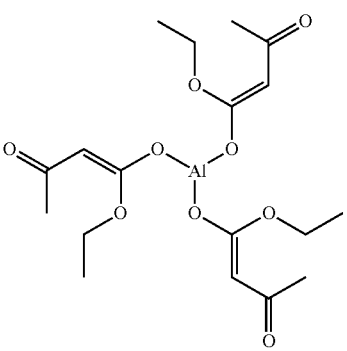

SL-4

(SL-5): Aluminum octadecylacetoacetate diisopropylate (trade name "PLENACT AL-M", manufactured by Ajinomoto Fine-Techno Co., Inc.)

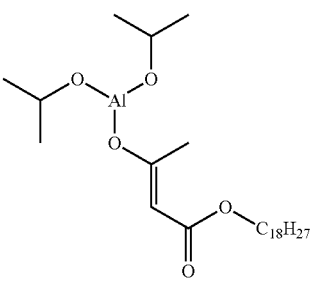

SL-5

<Zirconium Alkoxide Compound>

(SZ-1):

Zirconium tetra-n-propoxide (trade name "ORGATIX ZA-45", manufactured by Matsumoto Fine Chemical Co., Ltd.)

SZ-1

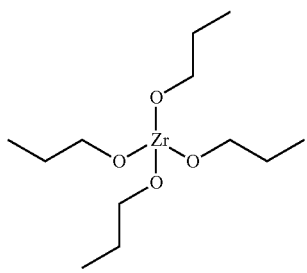

(SZ-2):

Zirconium tetra-n-butoxide (trade name "ORGATIX ZA-65", manufactured by Matsumoto Fine Chemical Co., Ltd.)

SZ-2

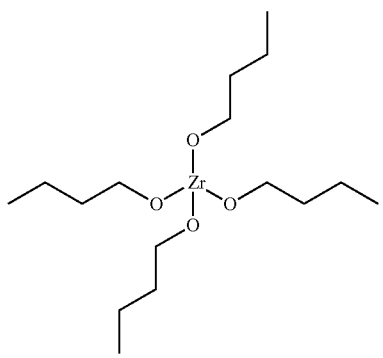

(SZ-3):

Zirconium tetraacetylacetonate (trade name "ORGATIX ZC-150", manufactured by Matsumoto Fine Chemical Co., Ltd.)

SZ-3

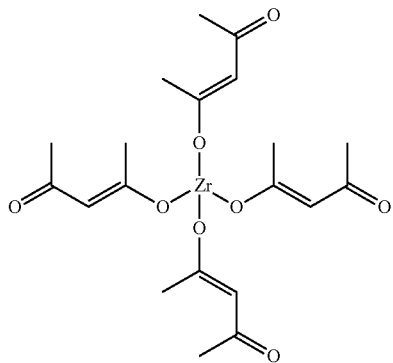

(SZ-4):

Zirconium lactate ammonium salt (trade name "ORGATIX ZC-300", manufactured by Matsumoto Fine Chemical Co., Ltd.)

SZ-4

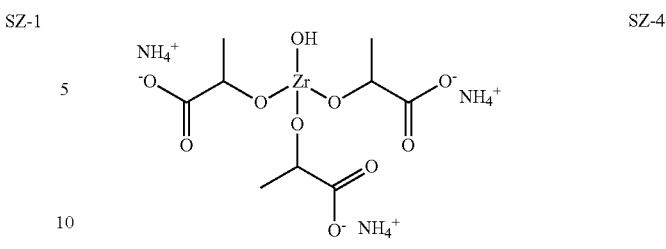

(SZ-5):

Zirconium stearate tributoxide (trade name "ORGATIX ZC-320", manufactured by Matsumoto Fine Chemical Co., Ltd.)

SZ-5

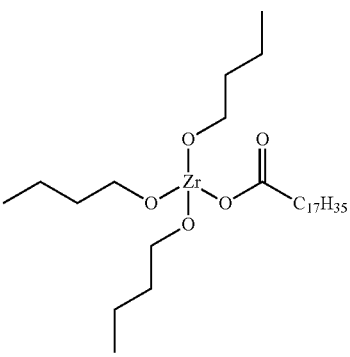

(SZ-6):

Zirconium tributoxy monoacetylacetonate (trade name "ORGATIX ZC-540", manufactured by Matsumoto Fine Chemical Co., Ltd.)

SZ-6

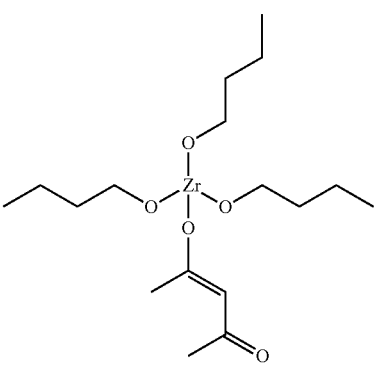

(SZ-7):

Zirconium dibutoxy bis(ethyl acetoacetate) (trade name "ORGATIX ZC-580", manufactured by Matsumoto Fine Chemical Co., Ltd.)

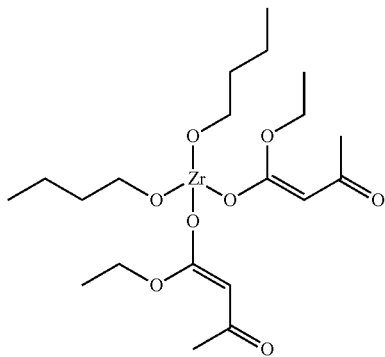

SZ-7

Surface Treatment Agent Used in Comparative Examples (SA-2): N-trimethoxysilylpropyl-N,N,N-trimethylammonium chloride (trade name "SIT8415.0", manufactured by Gelest, Inc., 50% methanol aqueous solution)
(SC-1): Methyltrichlorosilane (reagent manufactured by Tokyo Chemical Industry Co., Ltd.)
(SC-2): 1,1,1,3,3,3-hexamethyldisilazane (reagent manufactured by Tokyo Chemical Industry Co., Ltd.)
(SC-3): Vinyltrichlorosilane (reagent manufactured by Tokyo Chemical Industry Co., Ltd.)

Example 1

49.4 parts by mass of vinyl-terminated dimethylsiloxane copolymer (component (A) in Table 2 which will be given later, "DMS-V41" (trade name) manufactured by Gelest, Inc., weight-average molecular weight: 627,000), 0.6 parts by mass of methylhydrosiloxane polymer (component (B) in Table 2 which will be given later, "HMS-991" (trade name) manufactured by Gelest, Inc., weight-average molecular weight: 1,600, Si—H equivalent: 67 g/mol), and 50.0 parts by mass of surface-treated zinc oxide particles (C-1) (component (C) in Table 2 which will be given later) prepared in the foregoing Preparation Example were kneaded with a kneader at a temperature of 23° C. for 2 hours to obtain a uniform paste. A platinum catalyst solution (SIP6832.2, manufactured by Gelest, Inc., platinum concentration: 2%) was added at 500 ppm (10 ppm in terms of platinum) to the paste which was then mixed, defoamed under reduced pressure, placed in a 150 mm×150 mm metal mold, and heat-treated at 60° C. for 3 hours to obtain a silicone resin sheet having a thickness of 2.0 mm.

Silicone resin sheets of Examples 2 to 28 and Comparative Examples 1 to 6 were produced in the same manner as the silicone resin sheet of Example 1, except that the compositions shown in Table 2 which will be given later were adopted in the production of the silicone resin sheet of Example 1.

[Acoustic Velocity]

With regard to the obtained silicone resin sheet having a thickness of 2 mm, an acoustic velocity at 25° C. was measured using a sing-around acoustic velocity measurement apparatus (trade name "UVM-2" model, manufactured by Ultrasonic Engineering Co., Ltd.) in accordance with JIS Z2353 (2003) and evaluated by applying it to the following standards. An evaluation of "A" to "C" is acceptable in the present test.

<Evaluation Standards>

A: The acoustic velocity is less than 840 m/s
B: The acoustic velocity is 840 m/s or more and less than 870 m/s
C: The acoustic velocity is 870 m/s or more and less than 900 m/s
D: The acoustic velocity is 900 m/s or more

[Density and Acoustic Impedance]

With regard to the obtained silicone resin sheet having a thickness of 2 mm, the density at 25° C. was measured using an electronic hydrometer (trade name: "SD-200L", manufactured by Alfa Mirage Co., Ltd.) in accordance with the density measurement method of Method A (underwater substitution method) described in JIS K7112 (1999). The acoustic impedance was obtained from the product of the measured density and the above acoustic velocity, and evaluated by applying it to the following standards. An evaluation of "A" to "C" is acceptable in the present test.

<Evaluation Standards>

A: The acoustic impedance is 1.4 Mrayl or more
B: The acoustic impedance is 1.3 Mrayl or more and less than 1.4 Mrayl
C: The acoustic impedance is 1.2 Mrayl or more and less than 1.3 Mrayl
D: The acoustic impedance is less than 1.2 Mrayl

[Adhesion Test]

67 parts by mass of epoxy resin (bisphenol A diglycidyl ether, "jER828" manufactured by Mitsubishi Chemical Corporation, epoxy equivalent: 189 g/eq) and 33 parts by mass of amine-based curing agent ("jER CURE ST12" manufactured by Mitsubishi Chemical Corporation, amine value: 365 KOHmg/g) were mixed and poured into a mold and then cured at 80° C. for 12 hours to obtain an epoxy resin sheet having a length of 12 cm, a width of 12 cm, and a thickness of 2 mm.

The paste according to Example 1 was placed on the obtained sheet so as to have a length of 10 cm, a width of 2 cm, and a thickness of 0.4 mm, followed by heat-treating at 60° C. for 3 hours to obtain a laminated sheet in which the silicone resin sheet was adhered on the epoxy resin sheet. A test piece having a length of 8 cm and a width of 1 cm was cut out from the laminated sheet. Then, using a tensile tester (product name "3340" model, manufactured by Instron Corporation), the peel strength in a case where the silicone resin sheet was peeled off from the epoxy resin sheet at 90° was measured according to JIS K6864-1 (1999), and evaluated by applying it to the following standards. An evaluation of "A" to "C" is acceptable in the present test.

<Evaluation Standards>

A: The peel strength is 20 N/cm or more
B: The peel strength is 15 N/cm or more and less than 20 N/cm
C: The peel strength is 10 N/cm or more and less than 15 N/cm
D: The peel strength is less than 10 N/cm

[Test of Durability Against Hydrochloric Acid]

The obtained silicone resin sheet having a thickness of 2 mm was immersed in a 1% hydrochloric acid aqueous solution at 40° C. for one week (168 hours), washed with water, and dried at 23° C. for 24 hours. No. 3 dumbbell type test pieces were prepared by punching from the sheet before immersion and the sheet after immersion. A tensile test was carried out using the test pieces according to JIS K 7161-1: 2014. The retention rate of breaking strength (100×breaking strength of the test piece after immersion/breaking strength of the test piece before immersion (%)) was calculated and evaluated by applying it to the following standards. An evaluation of "A" to "C" is acceptable in the present test. The better the result of the present test, the better the durability against body fluid (gastric acid).

<Evaluation Standards>
A: The retention rate of breaking strength is 95% or more
B: The retention rate of breaking strength is 85% or more and less than 95%
C: The retention rate of breaking strength is 70% or more and less than 85%
D: The retention rate of breaking strength is less than 70%

TABLE 2

|  |  | EX 1 | EX 2 | EX 3 | EX 4 | EX 5 | EX 6 | EX 7 | EX 8 | EX 9 | EX 10 |
|---|---|---|---|---|---|---|---|---|---|---|---|
| Component (A) | Type | A-1 | A-1 | A-1 | A-1 | A-1 | A-1 | A-1 | A-1 | A-1 | A-1 |
|  | Content [% by mass] | 49.4 | 49.4 | 49.4 | 49.4 | 49.4 | 49.4 | 49.4 | 49.4 | 49.4 | 49.4 |
| Component (B) | Type | B-1 | B-1 | B-1 | B-1 | B-1 | B-1 | B-1 | B-1 | B-1 | B-1 |
|  | Content [% by mass] | 0.6 | 0.6 | 0.6 | 0.6 | 0.6 | 0.6 | 0.6 | 0.6 | 0.6 | 0.6 |
| Component (C) | Type | C-1 | C-3 | C-4 | C-5 | C-6 | C-7 | C-8 | C-9 | C-10 | C-11 |
|  | Average primary particle diameter [nm] | 35 | 35 | 35 | 35 | 35 | 35 | 35 | 35 | 35 | 35 |
|  | Surface treatment agent (S) | SA-1 | SM-1 | SM-2 | SI-1 | SI-2 | ST-1 | ST-2 | ST-3 | SL-1 | SL-2 |
|  | Treatment amount [php] | 30 | 30 | 30 | 30 | 30 | 30 | 30 | 30 | 30 | 30 |
|  | Content [% by mass] | 50.0 | 50.0 | 50.0 | 50.0 | 50.0 | 50.0 | 50.0 | 50.0 | 50.0 | 50.0 |
| Acoustic velocity |  | A | B | A | A | A | A | C | C | C | B |
| Adhesiveness |  | A | A | C | C | A | A | C | C | C | A |
| Durability against hydrochloric acid |  | B | C | A | A | C | C | B | A | A | B |

|  |  | EX 11 | EX 12 | EX 13 | EX 14 | EX 15 | EX 16 | EX 17 | EX 18 | EX 19 | EX 20 |
|---|---|---|---|---|---|---|---|---|---|---|---|
| Component (A) | Type | A-1 | A-1 | A-1 | A-1 | A-1 | A-1 | A-1 | A-1 | A-1 | A-1 |
|  | Content [% by mass] | 49.4 | 49.4 | 49.4 | 49.4 | 49.4 | 49.4 | 49.4 | 49.4 | 49.4 | 49.4 |
| Component (B) | Type | B-1 | B-1 | B-1 | B-1 | B-1 | B-1 | B-1 | B-1 | B-1 | B-1 |
|  | Content [% by mass] | 0.6 | 0.6 | 0.6 | 0.6 | 0.6 | 0.6 | 0.6 | 0.6 | 0.6 | 0.6 |
| Component (C) | Type | C-12 | C-13 | C-14 | C-15 | C-16 | C-17 | C-18 | C-19 | C-20 | C-21 |
|  | Average primary particle diameter [nm] | 35 | 35 | 35 | 35 | 35 | 35 | 35 | 35 | 35 | 35 |
|  | Surface treatment agent (S) | SL-3 | SL-4 | SL-5 | SZ-1 | SZ-2 | SZ-3 | SZ-4 | SZ-5 | SZ-6 | SZ-7 |
|  | Treatment amount [php] | 30 | 30 | 30 | 30 | 30 | 30 | 30 | 30 | 30 | 30 |
|  | Content [% by mass] | 50.0 | 50.0 | 50.0 | 50.0 | 50.0 | 50.0 | 50.0 | 50.0 | 50.0 | 50.0 |
| Acoustic velocity |  | A | A | A | B | B | B | B | B | B | A |
| Adhesiveness |  | A | A | A | B | B | B | B | B | A | A |
| Durability against hydrochloric acid |  | B | A | B | A | A | A | A | A | A | A |

TABLE 3

|  |  | EX 21 | EX 22 | EX 23 | EX 24 | EX 25 | EX 26 | EX 27 | EX 28 | EX 29 |
|---|---|---|---|---|---|---|---|---|---|---|
| Component (A) | Type | A-1 | A-1 | A-1 | A-1 | A-1 | A-1 | A-1 | A-2 | A-3 |
|  | Content [% by mass] | 49.4 | 49.4 | 49.4 | 49.4 | 49.4 | 64.3 | 34.5 | 49.5 | 48.1 |
| Component (B) | Type | B-1 | B-1 | B-1 | B-1 | B-1 | B-1 | B-1 | B-1 | B-2 |
|  | Content [% by mass] | 0.6 | 0.6 | 0.6 | 0.6 | 0.6 | 0.7 | 0.5 | 0.5 | 1.9 |
| Component (C) | Type | C-22 | C-23 | C-24 | C-25 | C-26 | C-21 | C-21 | C-21 | C-21 |
|  | Average primary particle diameter [nm] | 20 | 60 | 250 | 35 | 35 | 35 | 35 | 35 | 35 |
|  | Surface treatment agent (S) | SL-4 | SL-4 | SL-4 | SL-4 | SL-4 | SZ-7 | SZ-7 | SZ-7 | SZ-7 |
|  | Treatment amount [php] | 30 | 30 | 30 | 10 | 50 | 30 | 30 | 30 | 30 |
|  | Content [% by mass] | 50.0 | 50.0 | 50.0 | 50.0 | 50.0 | 35.0 | 65.0 | 50.0 | 50.0 |
| Acoustic velocity |  | A | A | B | B | A | B | A | A | A |
| Adhesiveness |  | A | A | B | C | B | B | B | A | B |
| Durability against hydrochloric acid |  | A | B | C | B | B | A | A | A | A |

|  |  | CEX 1 | CEX 2 | CEX 3 | CEX 4 | CEX 5 | CEX 6 |
|---|---|---|---|---|---|---|---|
| Component (A) | Type | A-1 | A-1 | A-1 | A-1 | A-1 | A-1 |
|  | Content [% by mass] | 98.8 | 49.4 | 49.4 | 49.4 | 49.4 | 49.4 |
| Component (B) | Type | B-1 | B-1 | B-1 | B-1 | B-1 | B-1 |
|  | Content [% by mass] | 1.2 | 0.6 | 0.6 | 0.6 | 0.6 | 0.6 |
| Component (C) | Type | — | Q-1 | C-2 | C-27 | C-28 | C-29 |
|  | Average primary particle diameter [nm] |  | 35 | 35 | 35 | 35 | 35 |
|  | Surface treatment agent (S) | — | — | SA-2 | SC-1 | SC-2 | SC-3 |
|  | Treatment amount [php] |  | 0 | 30 | 30 | 30 | 30 |
|  | Content [% by mass] |  | 50.0 | 50.0 | 50.0 | 50.0 | 50.0 |

TABLE 3-continued

| | | | | | | |
|---|---|---|---|---|---|---|
| Acoustic velocity | D | C | A | C | C | C |
| Adhesiveness | D | D | C | D | D | D |
| Durability against hydrochloric acid | D | D | D | D | D | D |

<Notes of tables>
"EX": Example
"CEX": Comparative Example
"Treatment amount [php]": 100 × parts by mass of surface treatment agent/100 parts by mass of zinc oxide
In Comparative Example 2, Q-1 (untreated zinc oxide) is described in the row of component (C) for comparison.
[Polysiloxane (A) having vinyl group]
A-1: polydimethylsiloxane containing vinyl groups at both terminals (trade name "DMS-V41", manufactured by Gelest, Inc., weight-average molecular weight: 62,700)
A-2: polydimethylsiloxane containing vinyl groups at both terminals (trade name "DMS-V46", manufactured by Gelest, Inc., weight-average molecular weight: 117,000)
A-3: phenyl group-containing polysiloxane containing vinyl groups at both terminals (trade name "PDV-0541", manufactured by Gelest, Inc., weight-average molecular weight: 60,000, diphenylsiloxy unit: 5 mol %)
[Polysiloxane (B) having Si—H group]
B-1: polymethylhydrosiloxane (trade name "HMS-991", manufactured by Gelest, Inc., weight-average molecular weight: 1,600, methylhydroxysiloxy unit: 100 mol %, Si—H equivalent: 67 g/mol)
B-2: methylhydrosiloxane-phenylmethylsiloxane copolymer (trade name "HPM-502", manufactured by Gelest, Inc., weight-average molecular weight: 4,500, methylhydroxysiloxy unit: 45 to 50 mol %, Si—H equivalent: 165 g/mol)

As is clear from Table 2, the silicone resin sheets produced using the compositions of Comparative Examples did not pass the adhesiveness and hydrochloric acid durability tests.

On the other hand, it can be seen that the silicone resin sheet produced by using the composition according to the embodiment of the present invention has a low acoustic velocity, is less likely to be peeled off from an acoustic matching layer, and has excellent durability against body fluids.

EXPLANATION OF REFERENCES

1: acoustic lens
2: acoustic matching layer
3: piezoelectric element layer
4: backing material
7: housing
9: cord
10: ultrasound probe

What is claimed is:
1. A composition for an acoustic lens comprising the following components (A) to (C):
(A) a polysiloxane having a vinyl group;
(B) a polysiloxane having two or more Si—H groups in a molecular chain thereof; and
(C) zinc oxide surface-treated with at least one surface treatment agent of an isocyanatosilane compound, a thiocyanatosilane compound, an aluminum alkoxide compound, a zirconium alkoxide compound, or a titanium alkoxide compound.

2. The composition for an acoustic lens according to claim 1,
wherein the surface treatment agent is at least one of the isocyanatosilane compound, the aluminum alkoxide compound, or the zirconium alkoxide compound.

3. The composition for an acoustic lens according to claim 1,
wherein the surface treatment agent is at least one of the aluminum alkoxide compound or the zirconium alkoxide compound.

4. The composition for an acoustic lens according to claim 1,
wherein the surface treatment agent is the aluminum alkoxide compound that includes an aluminum alkoxide compound containing at least one of an acetonato structure or an acetato structure.

5. The composition for an acoustic lens according to claim 1,
wherein the surface treatment agent is the aluminum alkoxide compound that includes at least one compound represented by General Formula (1),

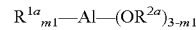            General Formula (1):

$R^{1a}{}_{m1}$—Al—$(OR^{2a})_{3-m1}$ where $R^{1a}$ represents a hydrogen atom, an alkyl group, a cycloalkyl group, an acyl group, an aryl group, or an unsaturated aliphatic group,
$R^{2a}$ represents a hydrogen atom, an alkyl group, a cycloalkyl group, an acyl group, an alkenyl group, an aryl group, a phosphonate group, or —$SO_2R^{S1}$, and RSI represents a substituent, and
m1 is an integer of 0 to 2.

6. The composition for an acoustic lens according to claim 1,
wherein the surface treatment agent is the zirconium alkoxide compound includes a zirconium alkoxide compound containing at least one of an acetonato structure or an acetato structure.

7. The composition for an acoustic lens according to claim 1,
wherein the surface treatment agent is the zirconium alkoxide compound that includes at least one compound represented by General Formula (2),

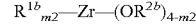            General Formula (2):

$R^{1b}{}_{m2}$—Zr—$(OR^{2b})_{4-m2}$ where $R^{1b}$ represents a hydrogen atom, an alkyl group, a cycloalkyl group, an acyl group, an aryl group, or an unsaturated aliphatic group,
$R^{2b}$ represents a hydrogen atom, an alkyl group, a cycloalkyl group, an acyl group, an alkenyl group, an aryl group, a phosphonate group, or —$SO_2R^{S2}$, and $R^{S2}$ represents a substituent, and
m2 is an integer of 0 to 3.

8. The composition for an acoustic lens according to claim 1,
wherein the surface treatment agent is the titanium alkoxide compound that includes a titanium alkoxide compound containing at least one atom of N, P, or S.

9. The composition for an acoustic lens according to claim 1,
wherein the surface treatment agent is the titanium alkoxide compound that includes at least one compound represented by General Formula (3),

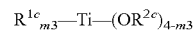            General Formula (3):

$R^{1c}{}_{m3}$—Ti—$(OR^{2c})_{4-m3}$ where $R^{1c}$ represents a hydrogen atom, an alkyl group, a cycloalkyl group, an acyl group, an aryl group, or an unsaturated aliphatic group, $R^{2c}$ represents a hydrogen atom, an alkyl group, a cycloalkyl group, an acyl group, an alkenyl group, an aryl group, a phosphonate group, or —$SO_2R^{S3}$, and $R^{S3}$ represents a substituent, and m3 is an integer of 0 to 3.

10. The composition for an acoustic lens according to claim 1,
wherein a content of the surface treatment agent in the component (C) is 1 to 100 parts by mass with respect to 100 parts by mass of the zinc oxide.

11. The composition for an acoustic lens according to claim 1,
wherein an average primary particle diameter of the zinc oxide constituting the component (C) is 10 to 200 nm.

12. An acoustic lens obtained by curing the composition for an acoustic lens according to claim 1.

13. An acoustic wave probe comprising the acoustic lens according to claim 12.

14. An ultrasound probe comprising the acoustic lens according to claim 12.

15. An acoustic wave measurement apparatus comprising the acoustic wave probe according to claim 13.

16. An ultrasound diagnostic apparatus comprising the acoustic wave probe according to claim 13.

17. A photoacoustic wave measurement apparatus comprising the acoustic lens according to claim 12.

18. An ultrasonic endoscope comprising the acoustic lens according to claim 12.

19. A method for manufacturing an acoustic wave probe, comprising forming an acoustic lens using the composition for an acoustic lens according to claim 1.

* * * * *